United States Patent
Lohse et al.

(10) Patent No.: US 11,352,393 B2
(45) Date of Patent: Jun. 7, 2022

(54) MYOTOXIN-NEUTRALIZING PEPTIDES

(71) Applicant: Brian Lohse, Copenhagen (DK)

(72) Inventors: Brian Lohse, Copenhagen (DK);
Andreas Hougaard Laustsen, Copenhagen N (DK); Ulate Julián Fernández, San José (CR); Saioa Oscoz Cob, Barcelona (ES); Vigliotti Bruno Lomonte, San José (CR); José Maria Gutiérrez Gutiérrez, San José (CR)

(73) Assignee: Brian Lohse, Copenhagen (DK)

( * ) Notice: Subject to any disclaimer, the term of this patent is extended or adjusted under 35 U.S.C. 154(b) by 0 days.

(21) Appl. No.: 17/040,743

(22) PCT Filed: Mar. 26, 2019

(86) PCT No.: PCT/EP2019/057522
§ 371 (c)(1),
(2) Date: Sep. 23, 2020

(87) PCT Pub. No.: WO2019/185593
PCT Pub. Date: Oct. 3, 2019

(65) Prior Publication Data
US 2021/0070804 A1 Mar. 11, 2021

(30) Foreign Application Priority Data
Mar. 27, 2018 (EP) .................... 18164297

(51) Int. Cl.
*A61K 38/00* (2006.01)
*C07K 7/08* (2006.01)
*A61P 39/02* (2006.01)

(52) U.S. Cl.
CPC ............... *C07K 7/08* (2013.01); *A61P 39/02* (2018.01); *A61K 38/00* (2013.01)

(58) Field of Classification Search
CPC ........ A61K 38/00; A61K 38/005; C07K 7/08; C07K 14/46; A61P 39/02
See application file for complete search history.

(56) References Cited

FOREIGN PATENT DOCUMENTS

WO           9512403         5/1995

OTHER PUBLICATIONS

Utkin et al. Animal venom studies: Current benefits and future developments. World J Biol Chem May 26, 2015; 6(2): 28-33 (Year: 2015).*
Gutierrez et al. Snakebite envenoming. Nature Reviews Disease Primers vol. 3: 17063 (2017) (Year: 2017).*
WHO accessed Aug. 20, 2021 at https://www.who.int/news-room/fact-sheets/detail/snakebite-envenoming. (Year: 2021).*
Umich.edu. Accessed on Aug. 20, 2021 at http://websites.umich.edu/~elements/web_mod/cobra/other.htm. Mechanism of antivenom (Year: 2021).*
Langenegger et al. Spider Venom: Components, Modes of Action, and Novel Strategies in Transcriptomic and Proteomic Analyses. Toxins 2019, 11,:611 (Year: 2019).*
Bruno Lomonte et al. "Neutralizing Interaction between Heparins and Myotoxin 11, aLysine 49 Phospholipase 4 from Bothrops asper Snake Venomtralizing Interaction between Heparins and Myotoxin 11, a Lysine 49 Phospholipase 4 from Bothrops asper Snake Venom", vol. 269, No. 47, (Nov. 25, 1994), pp. 29867-29873, Journal of Biological Chemistry, URL: http://www.jbc.org/content/269/47/29867.full.pdf#page=1&view=FitH, (Sep. 5, 2018), XP055504533 [A] 1-34.
James K Titus et al, "Application of phage display for the development of a novel inhibitor of PLA", Journal of Venom Research, England, (Jan. 1, 2017), pp. 19-24, URL: https://www.ncbi.nlm.nih.gov/pmc/articles/PMC5735792/pdf/JVR-08-19.pdf, (Sep. 5, 2018), XP055504512 [I] 1-34.
Laustsen Andreas Hougaard et al, "Pitfalls to avoid when using phage display for snake toxins", Toxicon, Elmsford, NY, US, (Dec. 23, 2016), vol. 126, doi:10.1016/J.TOXICON.2916.12.010, ISSN 0041-0101, pp. 79-89, XP029885315 [I] 1-34 * p. 87-p. 93; table 4.3.5.
Laustsen, Andreas Hougaard et al, "Recombinant Antivenoms", Copenhagen, University of Copenhagen, (2016), pp. 3, 86-93, ISBN 978-87-93086-61-6, XP002784726 [A] 1-34.
Rodríguez-Rodríguez Everardo Remi et al, "Broadening the neutralizing capacity of a family of antibody fragments against different toxins from Mexican scorpions", Toxicon, Elmsford, NY, US, (May 20, 2016), vol. 119, doi:10.1016/J.TOXICON.2016.05.011, ISSN 0041-0101, pp. 52-63, XP029665478 [A] 1-34.
Sergio Lizano et al, "Biochemical characterization and pharmacological properties of a phospholipase A 2 myotoxin inhibitor from the plasma of the snake Bothrops asper", Biochem. J, (Jan. 1, 1997), pp. 853-859, URL: https://www.ncbi.nlm.nih.gov/pmc/articles/PMC1218742/pdf/9307037.pdf, (Sep. 5, 2018), XP055503977 [A] 1-34.

* cited by examiner

*Primary Examiner* — Aradhana Sasan
*Assistant Examiner* — Mercy H Sabila
(74) *Attorney, Agent, or Firm* — Duane Morris LLP; Gregory M. Lefkowitz; Brandon A. Chan

(57) ABSTRACT

The present invention relates to polypeptides having myotoxin-neutralizing properties and their use for treatment of envenomation. The present invention further relates to methods for neutralizing a venom using the polypeptide of the invention as well as to methods of treatment of envenomation by administering said polypeptide to a subject in need thereof.

20 Claims, 13 Drawing Sheets

Specification includes a Sequence Listing.

Fig. 6

A Binding curve of TAMRA-JB006 to Myotoxin-II

B FP Increase in the absence of Myotoxin-II

Fig. 11

MYOTOXIN-NEUTRALIZING PEPTIDES

CROSS-REFERENCE TO RELATED APPLICATIONS

This application is a § 371 national stage entry of International Application No. PCT/EP2019/057522, filed Mar. 26, 2019, which claims priority of European Application No. 18164297.6, filed Mar. 27, 2018, the entire contents of which are incorporated herein by reference.

TECHNICAL FIELD

The present invention relates to polypeptides having myotoxin-neutralizing properties, in particular phospholipase $A_2$-neutralizing properties, and their use for treatment of envenomation. The present invention further relates to methods for neutralizing a venom using the polypeptide of the invention as well as to methods of treatment of envenomation by administering said polypeptide to a subject in need thereof.

BACKGROUND

Snakebites constitute a public health hazard of high impact in Asia, Africa, Latin America, and parts of Oceania. Parenteral administration of animal-derived antivenoms currently constitutes the cornerstone of the therapy of snakebite envenoming. However, despite well-demonstrated efficacy and safety of many antivenoms worldwide, they are still being produced by traditional animal immunization procedures, and therefore present a number of drawbacks. Technological advances within biopharmaceutical development and medicinal chemistry could pave the way for rational drug design approaches against snake toxins. This could minimize the use of animals during antivenom production and bring forward more effective therapies for snakebite envenomings. Furthermore, despite their public health relevance, the current technologies used for antivenom manufacture present a number of limitations: (a) Since antivenom antibodies, or antibody fragments, are of animal origin, they may elicit early and late adverse reactions in the human or animal recipients. (b) Only a fraction of antivenom antibodies, ranging from 5-36%, are directed towards venom antigens, thus implying that the treated snakebite victim receives a large surplus of 'irrelevant' antibodies, which increase the likelihood of adverse reactions. (c) Antivenoms are relatively inefficient in neutralizing the toxins responsible for the local pathological effects in envenomings by viperid and some elapid snake species, owing to the rapid development of these effects after the bite and to the pharmacokinetic properties of antibodies. (d) Since antivenoms are generated from pools of plasma of groups of immunized animals, batch-to batch variation is inherent to the manufacturing process.

Thus, there is an urgent need to explore and develop novel strategies to generate improved antivenoms and novel toxin inhibitory compounds.

SUMMARY

In this context, a window of opportunity has emerged to apply modern medicinal chemistry and biotechnological approaches in the development of new generation snakebite therapies of higher efficacy and safety. The merging of these approaches with the growing body of scientific knowledge on snake venom composition and mechanisms of action brings a unique possibility to undertake a leap forward in the treatment of snakebite envenoming.

The present invention addresses these challenges of the current treatments of envenomation. More specifically, the present invention relates to the challenges posed by treatment of envenomation caused by myotoxins, for example a phospholipase $A_2$, such as the need for quick first aid treatments, preferably in the field. The inventors have surprisingly identified polypeptides, generated from a phage display library containing random sequence polypeptides, which possess myotoxin-neutralizing properties. The inventors have demonstrated that the polypeptides of the invention are capable of neutralizing myotoxins both in vitro and in vivo.

Thus, the present invention relates to polypeptides having myotoxin-neutralizing properties and to their use in treatment of envenomation. The present polypeptides are preferably non-natural and are preferably not derived from any naturally occurring antivenom proteins or fragments thereof. Without being bound by theory, advantages of the polypeptide include the formulation of a product based on a single active pharmaceutical ingredient with improved and more scalable production and quality control processes (e.g. avoiding variability resulting from the use of domestic animals as production vehicles, potential higher stability of polypeptides and more) as compared to the currently used antibody antivenoms. Furthermore, the polypeptides of the invention may be administered in formulations which are simple to use, allowing for first aid treatment of envenomation in the field, which is an important aspect for prevention of muscle tissue loss, permanent sequelae and death. The polypeptides of the present invention may therefore be highly valuable for treatment of envenomation, addressing several of the issues of the currently available treatment such as less adverse effects e.g. due to a more focused, targeted and efficacious treatment with administration of no 'irrelevant' pharmaceutical ingredients, better treatment of local pathological effects in envenomings, and less batch to batch variation.

In one aspect, the present invention provides polypeptides having myotoxin-neutralizing properties.

In a second aspect, the present invention provides a method for neutralizing a venom by contacting a polypeptide of the present invention to said venom.

In a third aspect, the present invention provides a method for treatment of envenomation, said method comprising administering to a subject in need thereof a therapeutically effective amount of a polypeptide of the present invention.

Since this viral DNA contains the sequence for the peptide on the virion surface, the DNA sequencing will reveal which peptide bound to the target.

Figure 1:
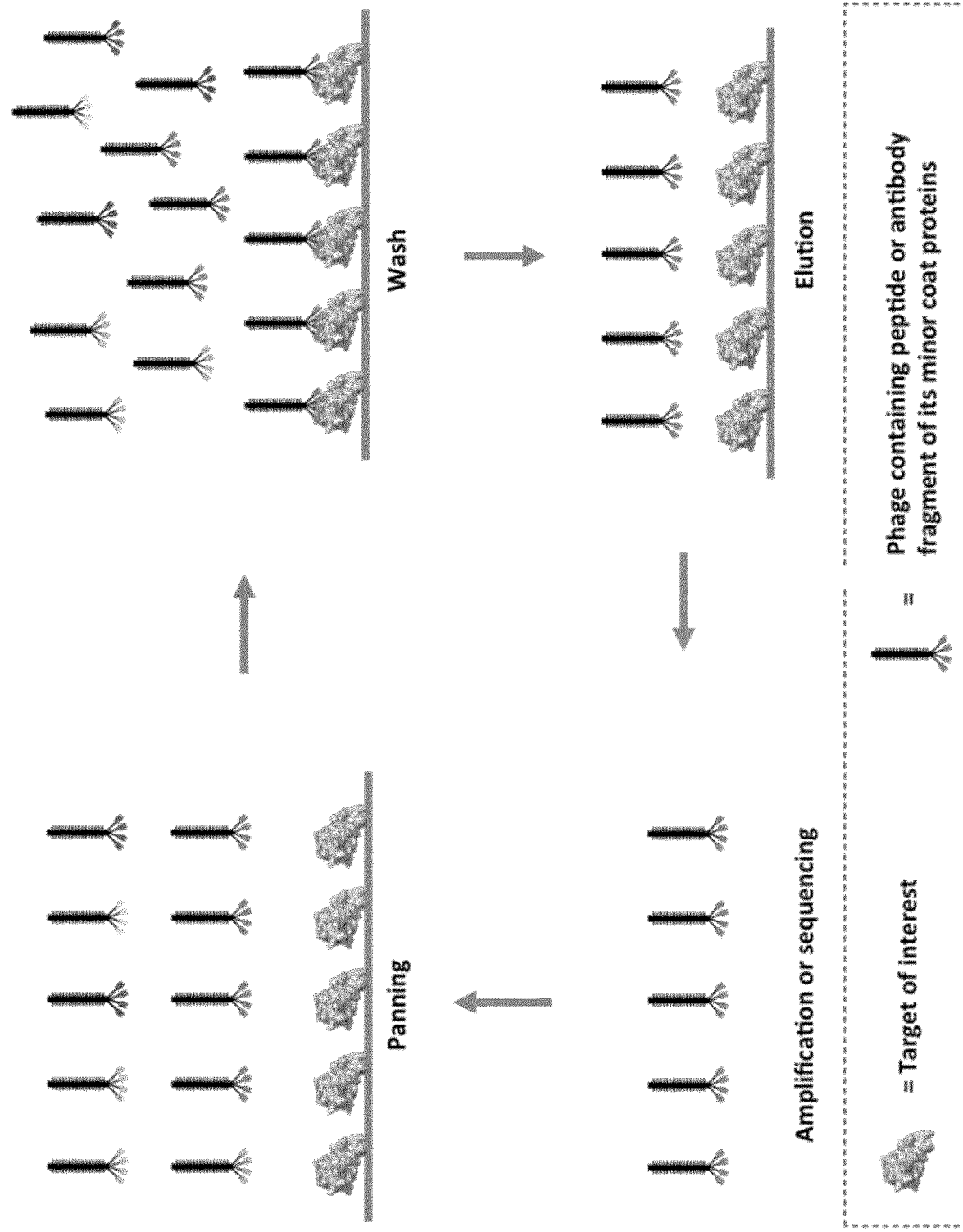
FIG. 1. Schematic illustration of the process of phage display screening. Phage display involves expression of a library of peptides engineered to take place on the surface of a phage virion (virus particle), while the DNA encoding each individual peptide variant is carried inside the virion. Typically, a phage display library containing several million different virions that each have a unique peptide on its outside is constructed. The target of interest is coated onto the surface of a well (microtiter plate) and a library of virions with peptides on their surface is panned onto the well. This allows strongly binding virions to stick to the bound target, while non-binding virions will be washed away. After a few iterative panning cycles, the strongly binding virions are eluted, and their DNA is sequenced.
Figure 2:
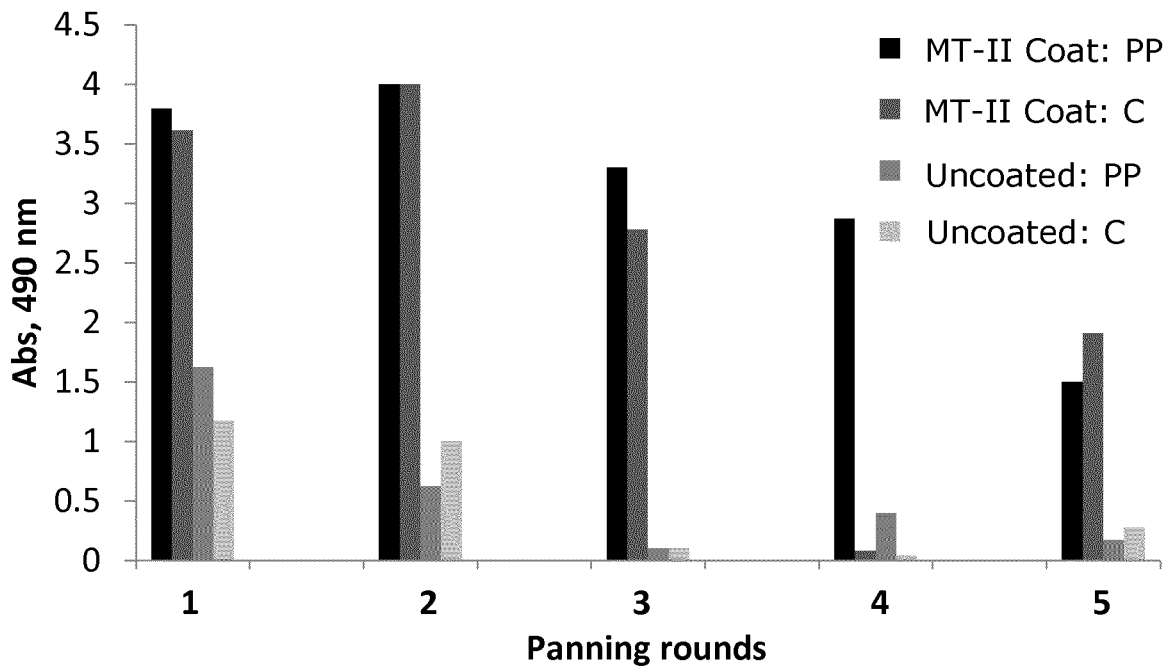

FIG. 2. ELISA results from the polyclonal phage libraries of the five panning rounds with 16- and 20-mer library (phage precipitated (PP)). Black bars represent the signal from wells coated with myotoxin II and tested against PP library (MT-II Coat: PP). Dark grey bars represent signal from wells coated with myotoxin II, tested against control library (MT-II Coat: C). Medium grey bars represent signal from uncoated wells, tested against PP (Uncoated: PP), and light grey bars represent signals from uncoated wells tested against control library (Uncoated: C).

Figure 3:
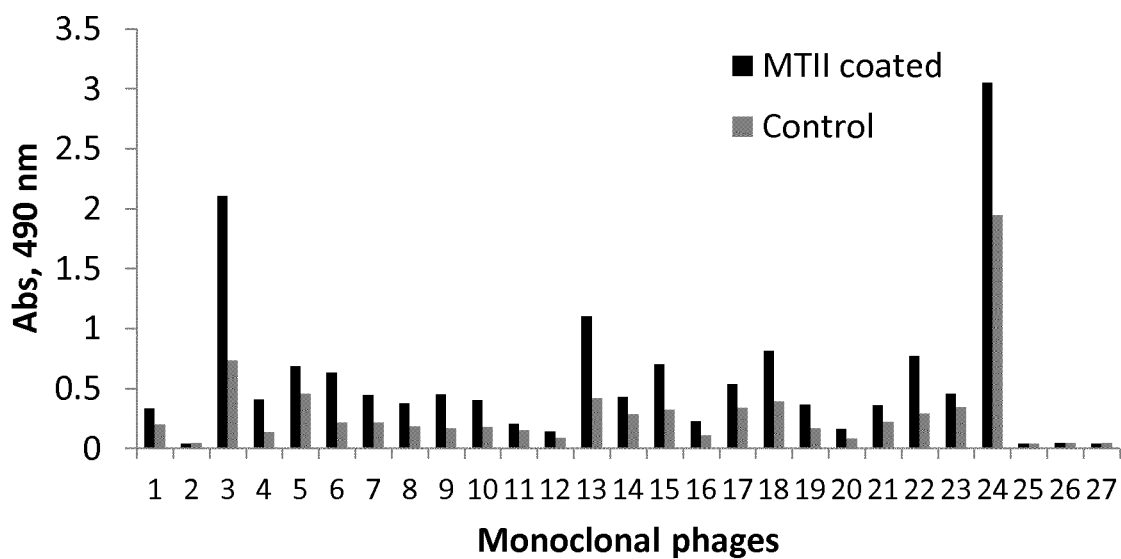

FIG. 3. ELISA results from 27 randomly selected clones from 4th panning rounds. Black bars represents signal from wells coated with myotoxin II (MT-II coated), and grey bars represent signal from uncoated control wells (Control).

Figure 4:
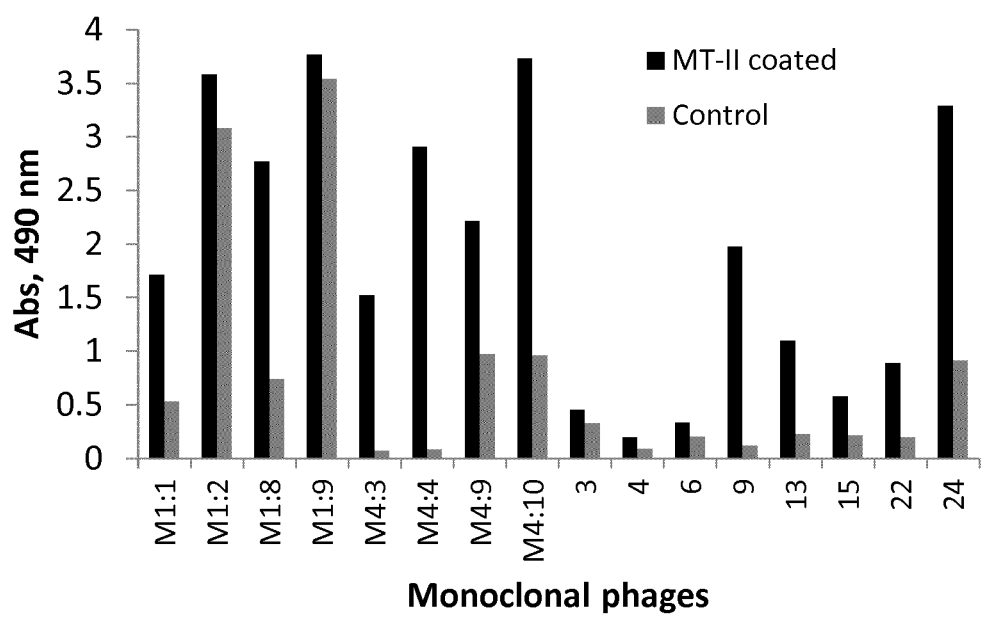

FIG. 4. ELISA results from 16 selected monoclonal phages. Black bars represents signal from wells coated with myotoxin II (MT-II coated), grey bars represents signal from uncoated wells (Control).

Figure 5:
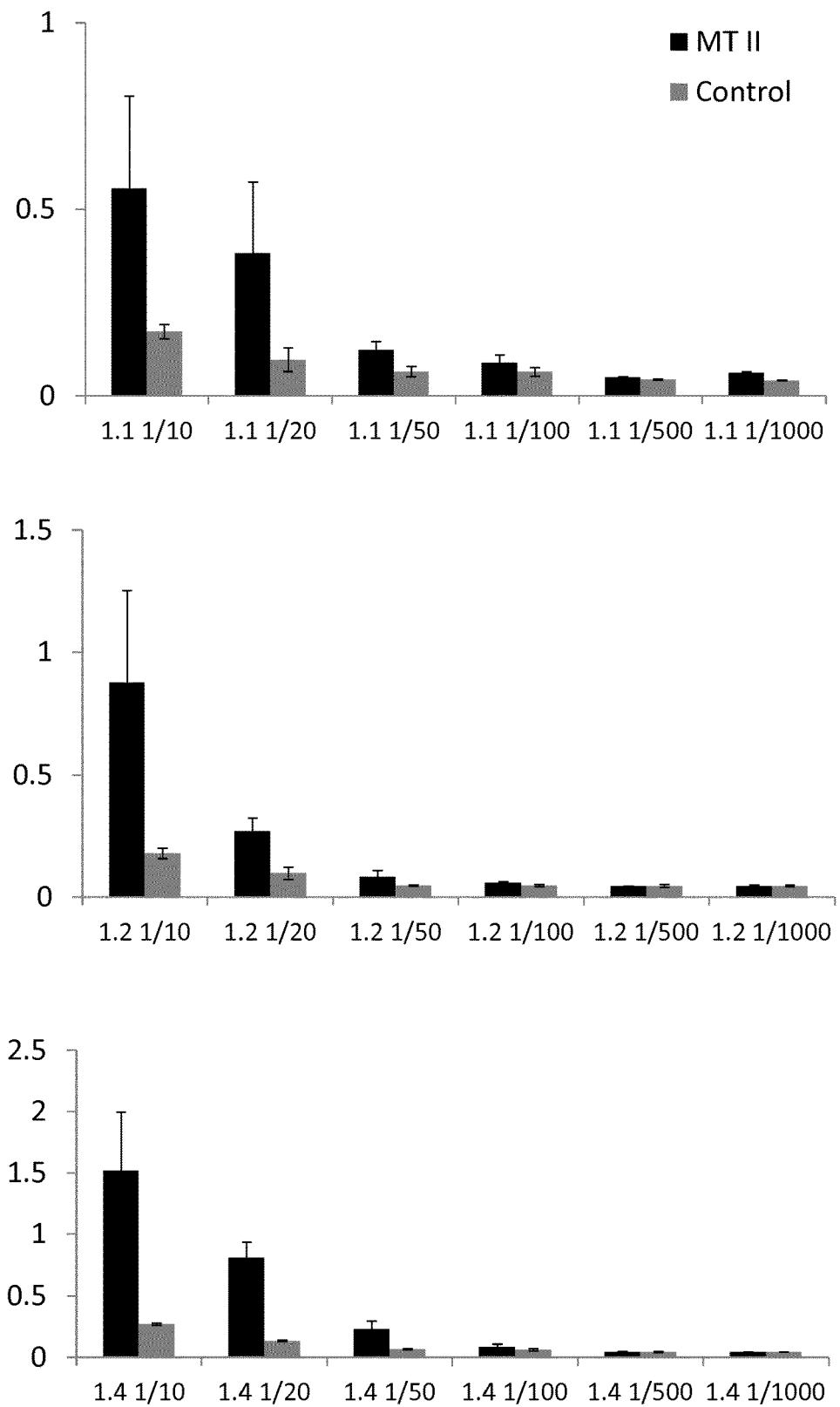
Figure 5:
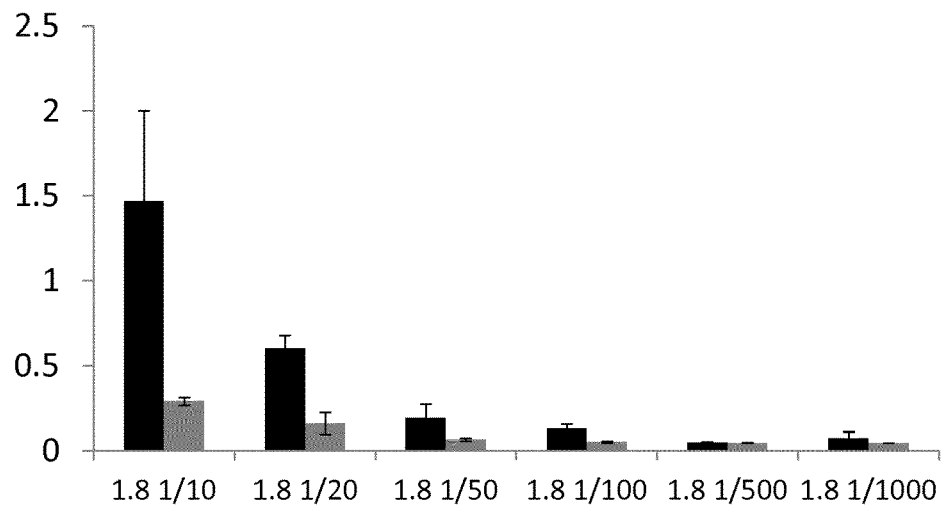
Figure 5:
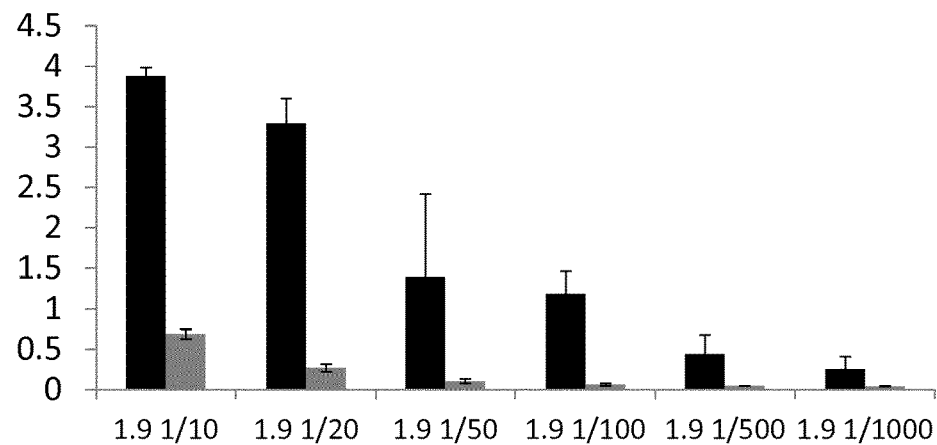
Figure 5:
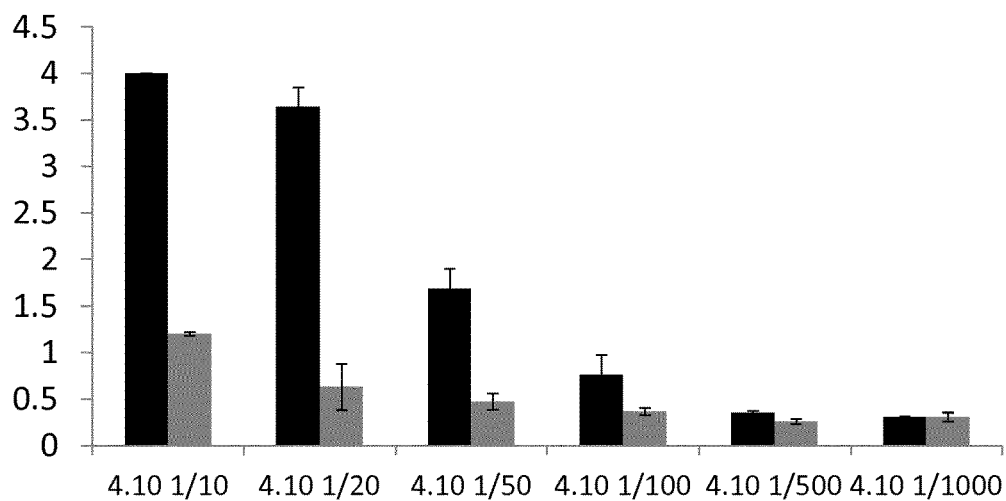

FIG. 5. Graphs showing binding of clones 1.1, 1.2, 1.4, 1.8, 1.9 and 4.10 to myotoxin II at different dilutions. Black bars are representing signals from wells coated with myotoxin II (MT II), grey bars representing signals from uncoated wells (Control). Results are shown as average value from triplicate results. Error bars showing standard deviation.

Figure 6:
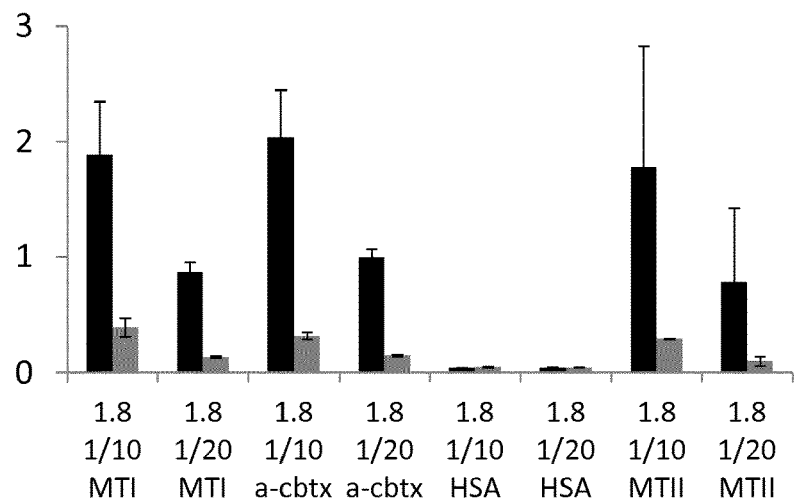
Figure 6:
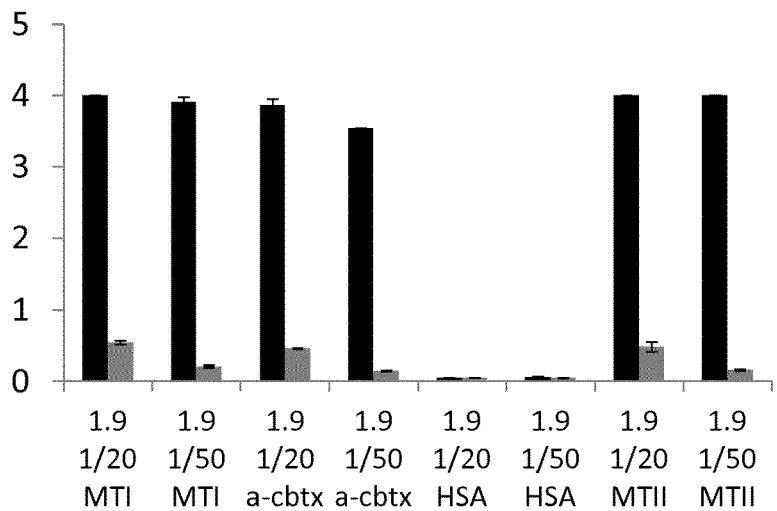
Figure 6:
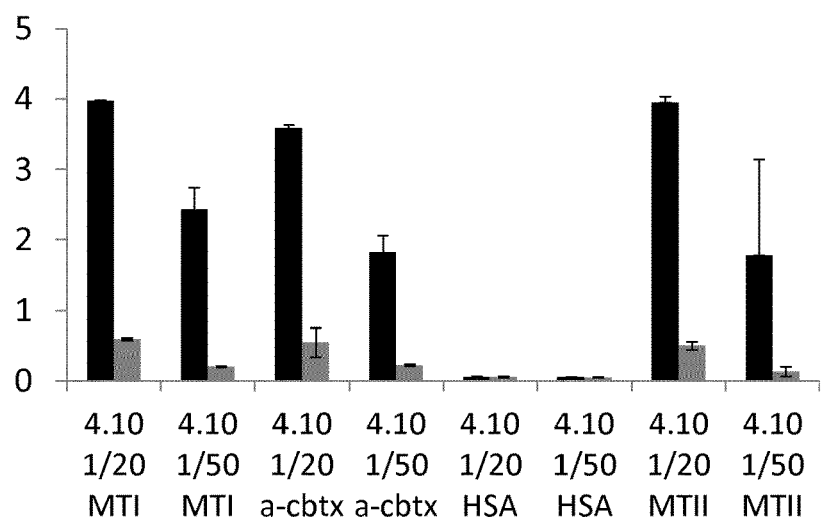

FIG. 6. Cross reactivity of selected monoclonal phages against different toxins as analysed by ELISA. Black bars represent signal from wells coated with myotoxin I (MT-I), α-cobra toxin (a-cbtx), human serum albumin (HSA), or myotoxin II (MTII), respectively. Grey bars represent signals from uncoated wells (Control). Results are shown as average value from triplicate results. Error bars showing standard deviation of triplicate results.

Figure 7:
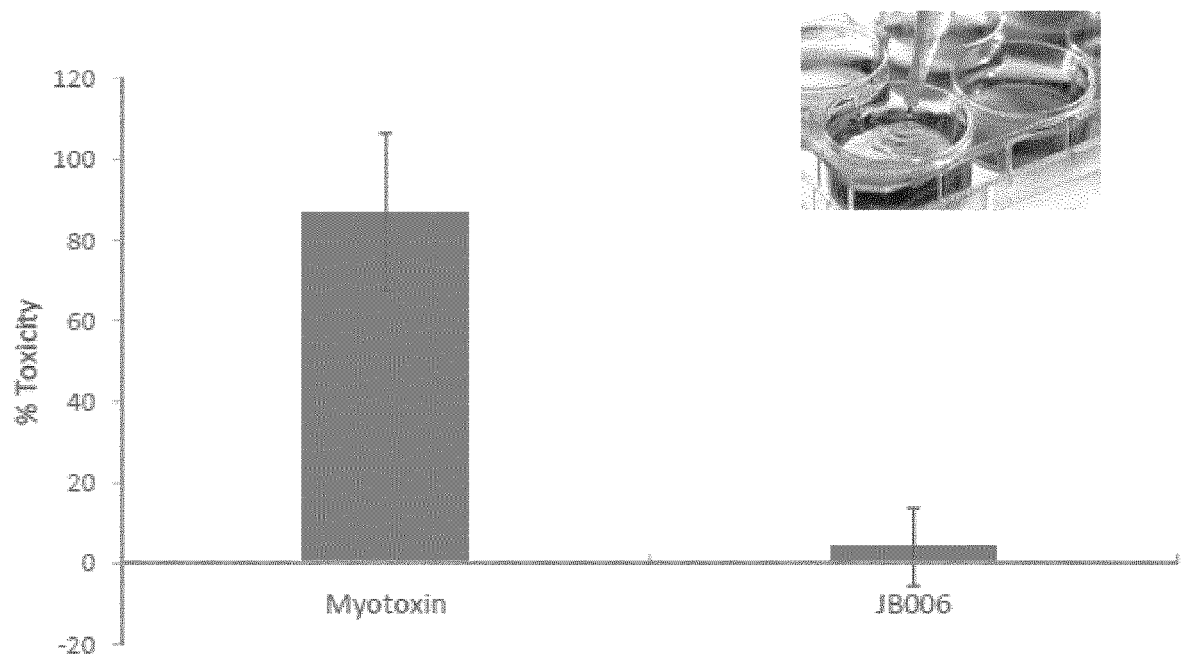

FIG. 7. Myogenic C2C12 cell toxicity of myotoxin alone or in the presence of peptide 1.9 (SEQ ID NO: 5). A concentration of 900 µM peptide 1.9 (SEQ ID NO: 5) almost completely neutralizes myotoxin II toxicity in cells. Results are shown as average value from triplicate results. Error bars showing standard deviation of triplicate results.

Figure 8:
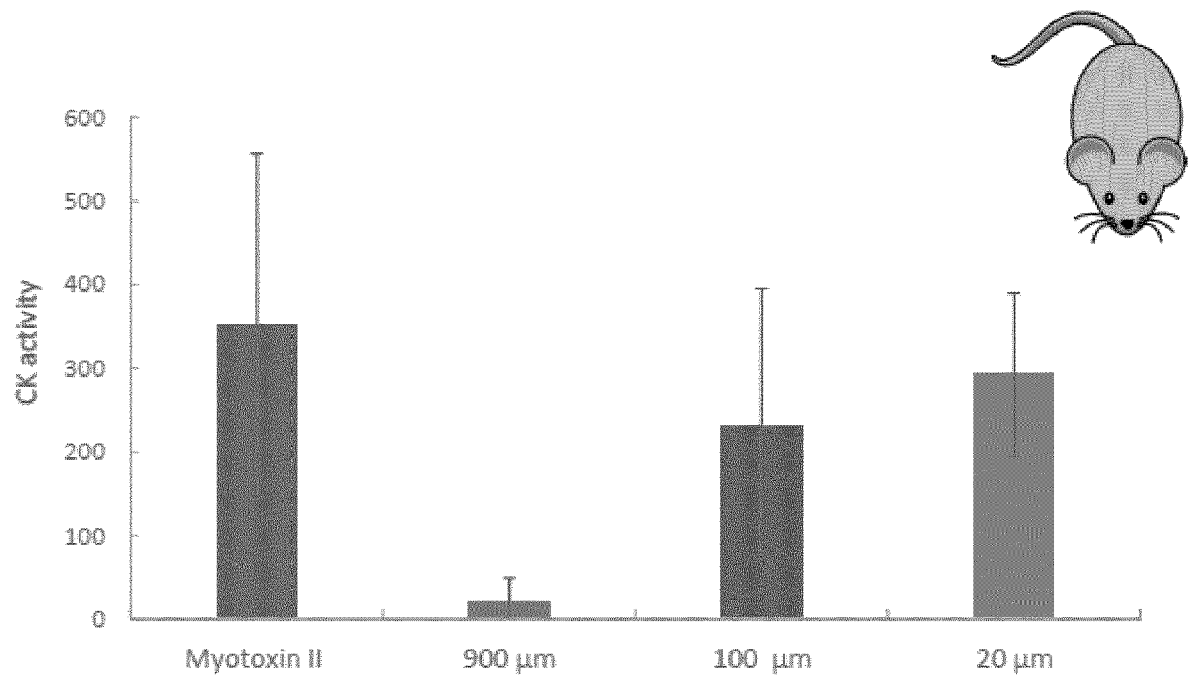

FIG. 8. Plasma Creatine Kinase (CK) activity in mice treated with myotoxin II alone or in the presence of increasing amounts of peptide 1.9 (SEQ ID NO: 5). A concentration of 900 µM peptide 1.9 (SEQ ID NO: 5) almost completely neutralizes myotoxin II toxicity in a mouse model as seen by the low CK activity. Results are shown as average value from five replicates, with error bars showing standard deviation of triplicate results.

Figure 9:
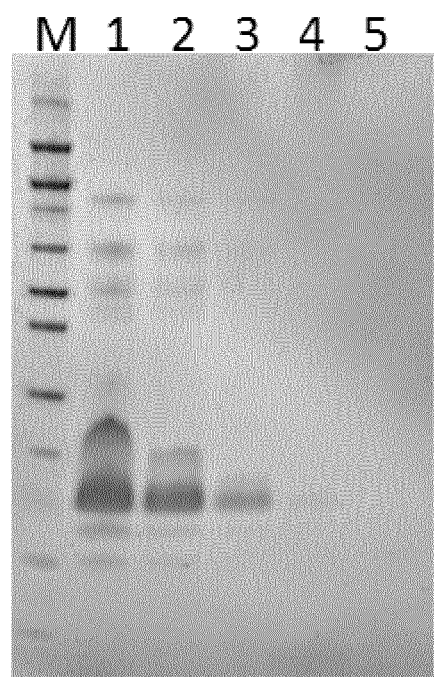

FIG. 9. SDS-PAGE of *B. asper* venom (lane 2), run through from overnight incubation (lane 3), 1$^{st}$ elution (lane 4) and 2$^{nd}$ elution (lane 5) stained with Coomassie blue. M: molecular weight marker.

Figure 10:
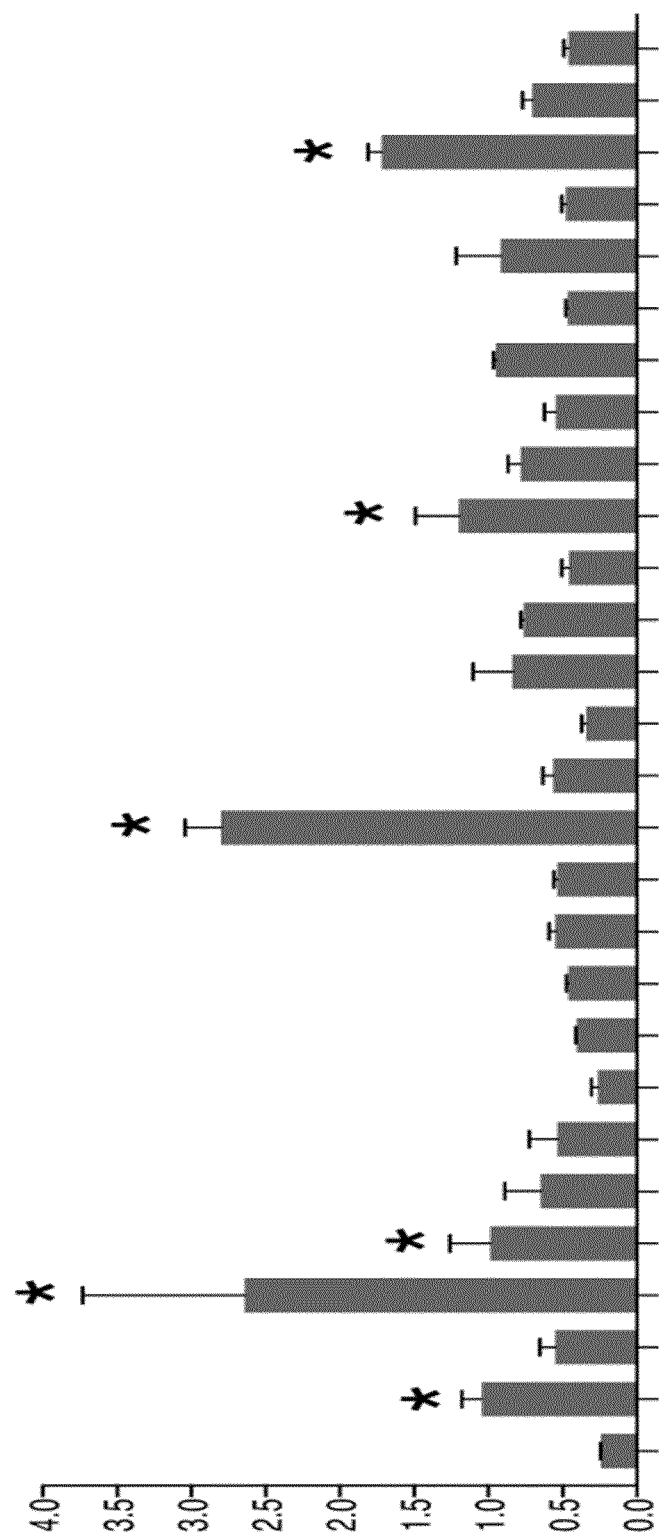

FIG. 10. ELISA cross affinity screen using JB006 expressing phages. The experiment was performed in duplicate and the error bars are the standard deviation. *Signals with a ratio of signal/control >4 are highlighted. On the X-axis, left to right: control (no protein); *Lachesisis muta muta; Bitis arietans* (male tanz.); *Bothrops asper; Dendroaspis polylepis; Naja kaouthia; Crotalus durissus; A. laevis; Ammodytes meridionalis; V. ammodytes; C. atrox; M. bulgardahica*; Myotoxin II; *D. russelli; V. kaznakovi; M. nigrocinctus; Crotalus cerastes; Bothriechis lateralis; Bitis caudalis; Crotalus adamanteus; Bitis parviocula; Cerastes cerastes; Bitis nasicornis; Bitis rhinoceras; O. microlepidotus; A. nummifer mexicanus; B. schlegelli; A. picadoi.*

Figure 11:
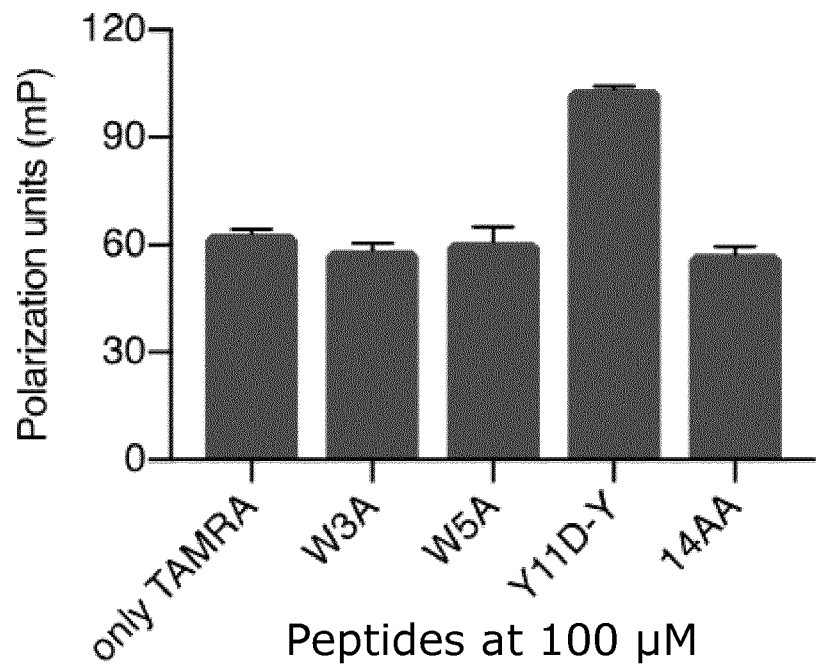

FIG. 11. Fluorescence polarization (FP) binding assay to investigate JB006. A Binding curve of TAMRA-labeled JB006 to Myotoxin-11. B Increase of FP signal when mixing TAMRA-JB006 at different concentrations of JB006 in the absence of Myotoxin-11. C All non-aggregating peptides were not able outcompete the TAMRA-JB006 probe bound to Myotoxin-II.

Figure 12:
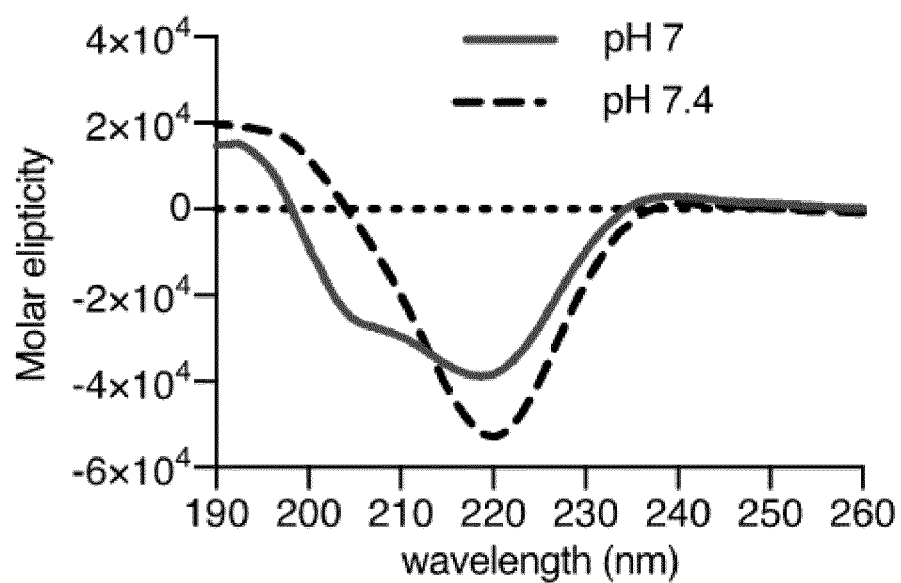
Figure 12:
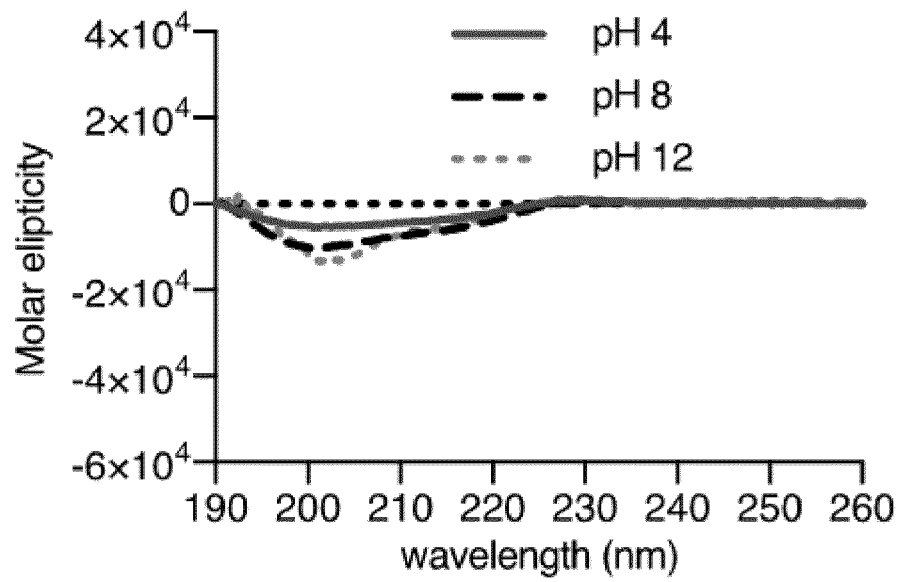
Figure 12:
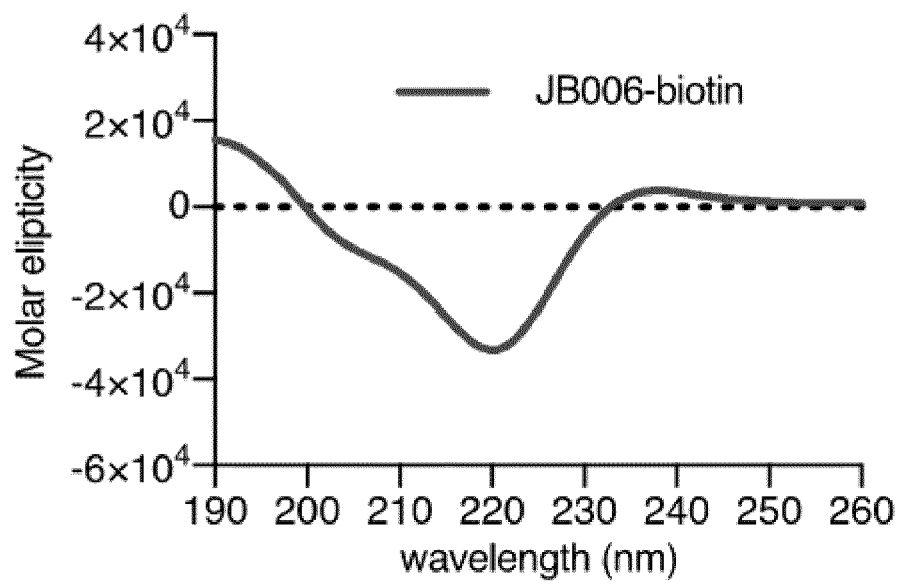

FIG. 12. Circular dichroism (CD) spectra of JB006 and analogues. A CD spectra of JB006 at neutral pH values show helical structure content. B JB006 is unstructured at pH values of 4, 8 and 12. C Biotinylated JB006 has a helical signature at neutral pH with minima at 208 nm and 220 nm.

DETAILED DESCRIPTION

The present invention relates to polypeptides having myotoxin-neutralizing properties and to their use in treatment of envenomation. The term 'myotoxin-neutralizing' as used herein in reference to a polypeptide, refers to the ability of said polypeptide to impact the effects of a myotoxin, for example the ability to remove or inhibit the toxicity of a myotoxin.

Myotoxins are a class of toxins found in venom of different species, such as snake venoms and lizard venoms. Myotoxins act upon skeletal muscle fibers inducing severe muscle necrosis. These toxins act very quickly, hence, instant treatment of envenomation caused by myotoxins is highly important in order to prevent muscle tissue loss and permanent sequelae and death.

The polypeptides of the invention are highly suitable for such instant treatment of envenomation, without being bound by theory due to their potential higher stability and multiple possible administration routes. A high stability is important in relation to e.g. transport, storage (in particular to avoid the cold-chain, necessary for current liquid antivenoms) and use of the anti-venom polypeptides outside of hospital settings, e.g. in the field, hence ensuring a prompt therapy before the patient reaches the hospital. Furthermore, the multiple administration routes allows for preparation of formulations which are simple to use and which can be used as first aid treatment in the field, e.g. by intramuscular administration using a pen or autoinjector. The polypeptides may be prepared with low batch to batch variation and be administered as single active pharmaceutical ingredients (APIs) resulting in more focused, specific and efficacious treatment and less adverse effects.

Herein are provided isolated non-naturally occurring polypeptides having myotoxin-neutralizing properties. Also provided are polynucleotides encoding such polypeptides, as well as vectors comprising said polynucleotides and phages comprising said polypeptides. Also provided is a host cell expressing said polypeptides or comprising said polynucleotides, vectors or phages. Also provided is a composition comprising the polypeptides disclosed herein.

Also provided is a method of neutralizing a venom comprising contacting a polypeptide, a polynucleotide, a vector, a phage, a host cell or a composition as disclosed herein with said venom.

Also provided is a method of improving antivenom therapy by co-administering a polypeptide, a polynucleotide, a vector, a phage, a host cell or a composition as disclosed herein with one or more additional antivenoms to a subject in need thereof.

Also described is the use of a polypeptide, a polynucleotide, a vector, a phage, a host cell or a composition as disclosed herein for the manufacture of a medicament, particularly for treating envenomation in a subject in need thereof.

Also provided herein is a method of treatment of envenomation, the method comprising administering to a subject in need thereof a therapeutically effective amount a polypeptide, a polynucleotide, a vector, a phage, a host cell or a composition as disclosed herein.

Method of Neutralizing a Venom

Herein is provided a method of neutralizing a venom, said method comprising contacting a polypeptide, a polynucleotide, a vector, a phage, a host cell or a composition comprising the polypeptide as described herein to said venom.

In one embodiment, the venom comprises a myotoxin.

Myotoxins are one class of toxins which can be divided into three structural groups:
  (a) the "small" myotoxins: these are basic, non-enzymatic polypeptides in single chain, of 42-45 amino acids, found so far only in the venoms of different species of rattlesnakes (*Crotalus, Sistrurus*), family Viperidae, subfamily Crotalinae
  (b) the "cardiotoxins/cytotoxins": these are basic, non-enzymatic single chain polypeptides of ~60 amino acids, that belong to the "three-finger toxin" family of proteins, found in many snakes of the family Elapidae in Africa and Asia.
  (c) the phospholipases $A_2$ (PLA2s): these are ~117-124 amino acid long proteins found in both the Elapidae and the Viperidae families of snakes. These can be further divided into two families; the group I PLA2s, and the group II PLA2s. Within the group II PLA2s, two subtypes exist; one which is very similar in structure to enzymatically-active PLA2s, but have lost the enzymatic activity. Still these are myotoxic, using a mechanism that obviously does not rely on catalysis. These natural variant subtypes are known as the "Lys49 PLA2 homologues". The other subtype is the "normal" PLA2s with enzymatic activity, these are known as the "Asp49 PLA2s".

An example of a Lys49 PLA2 homologue is Myotoxin II. An example of an Asp49 PLA2s is Myotoxin I.

In one embodiment, the venom comprises a phospholipase $A_2$ (PLA2). The phospholipase $A_2$ may be myotoxic, nephrotoxic, neurotoxic and/or cytotoxic. In one embodiment, the phospholipase $A_2$ is myotoxic.

In one embodiment, the venom comprises a phospholipase $A_2$ belonging to the group II PLA2s.

In one embodiment, the venom comprises a phospholipase $A_2$ selected from the group consisting of Lys49 PLA2 homologue and Asp49 PLA2s.

In one embodiment, the venom comprises a phospholipase $A_2$ which is a Lys49 PLA2 homologue.

In one embodiment, the venom comprises myotoxin I and/or myotoxin II.

In one embodiment, the venom comprises myotoxin II.

In some embodiments, the venom is selected from the group consisting of snake venom, lizard venom, insect venom, jellyfish venom, scorpion venom and cone snail venom.

In a preferred embodiment, the venom is selected from the group consisting of snake venom, spider venom, scorpion venom and bee venom. More preferably, the venom is a snake venom.

In one embodiment, the venom is from a snake, such as from a viperidae, for example from a *Bothrops* species, a *Agkistrodon* species, a *Protobothrops* species, a *Lachesis* species such as *Lachesis muta muta*, a *Bitis* species such as *Bitis caudalis*, an *Atropoides* species such as *Atropoides nummifer mexicanus* or a *Trimeresurus* species; from a sea snake, for example from an *Aipsurus laevis*; or from a land elapid, for example from a *Micrurus* species such as *Micrurus nigrocinctus* or from a *Dendroaspis* species such as *Dendroaspis polyepis*. Preferably, the venom is from a *Bothrops* species, more preferably from *Bothrops asper*. In preferred embodiments, the venom is from a snake selected from the group consisting of *Bitis caudalis, Atropoides nummifer mexicanus, Apisurus laevis, Lachesis muta muta, Micrurus nigrocintus, Dendroaspis polyepis* or *Bothrops asper*, most preferably the venom is from *Bitis caudalis, Atropoides nummifer mexicanus, Lachesis muta muta, Dendroaspis polyepis* or *Bothrops asper*.

The neutralization of said venom may take place in vivo. Thus, said method of neutralizing a venom may comprise the steps of administering a therapeutically effective amount of a polypeptide, a polynucleotide, a vector, a phage, a host cell or a composition as described herein to a subject in need thereof. The subject in need thereof may be an individual which is subject to envenomation. The subject in need thereof may be a human or an animal, such as for example a cat, dog, cattle, horse, llama, alpaca or sheep. The administered polypeptide, polynucleotide, vector, phage, host cell or composition as described herein may neutralize the venom causing said envenomation, thus serve as a treatment of said envenomation.

The neutralization of said venom may alternatively take place in vitro. Thus, said method of neutralizing a venom may comprise the steps of contacting an isolated venom in vitro with any polypeptide, polynucleotide, vector, phage, host cell or composition as described herein.

In particular, the method of neutralizing a venom comprises the step of contacting venom with a polypeptide comprising or consisting of an amino acid sequence selected from the group consisting of
  a) the amino acid sequence according to SEQ ID NO: 1, SEQ ID NO: 2, SEQ ID NO: 3, SEQ ID NO: 4, SEQ ID NO: 5, or SEQ ID NO: 6;
  b) a variant of SEQ ID NO: 1, SEQ ID NO: 2, SEQ ID NO: 3, SEQ ID NO: 4, SEQ ID NO: 5, or SEQ ID NO: 6, wherein said variant has at least 80% sequence identity to SEQ ID NO: 1, SEQ ID NO: 2, SEQ ID NO: 3, SEQ ID NO: 4, SEQ ID NO: 5, or SEQ ID NO: 6;
  c) a variant of SEQ ID NO: 1, SEQ ID NO: 2, SEQ ID NO: 3, SEQ ID NO: 4, SEQ ID NO: 5, or SEQ ID NO: 6, wherein said variant has between 1 and 10 amino acid substitutions and/or deletions as compared to SEQ ID NO: 1, SEQ ID NO: 2, SEQ ID NO: 3, SEQ ID NO: 4, SEQ ID NO: 5, or SEQ ID NO: 6;
  d) a fragment of SEQ ID NO: 1, SEQ ID NO: 2, SEQ ID NO: 3, SEQ ID NO: 4, SEQ ID NO: 5, or SEQ ID NO: 6, or a variant thereof having between 1 and 10 amino acid substitutions and/or deletions as compared to SEQ ID NO: 1, SEQ ID NO: 2, SEQ ID NO: 3, SEQ ID NO: 4, SEQ ID NO: 5, or SEQ ID NO: 6, such as between 1 and 5, for example between 1 and 3 amino acid substitutions and/or deletions as compared to SEQ ID NO: 1, SEQ ID NO: 2, SEQ ID NO: 3, SEQ ID NO: 4, SEQ ID NO: 5, or SEQ ID NO: 6;
  e) a fragment of SEQ ID NO: 1, SEQ ID NO: 2, SEQ ID NO: 3, SEQ ID NO: 4, SEQ ID NO: 5, or SEQ ID NO: 6, or a variant thereof having between 3 and 18 consecutive amino acids as compared to SEQ ID NO: 1, SEQ ID NO: 2, SEQ ID NO: 3, SEQ ID NO: 4, SEQ ID NO: 5, or SEQ ID NO: 6, such as between 5 and 15, for example between 7 and 12 consecutive amino acids as compared to SEQ ID NO: 1, SEQ ID NO: 2, SEQ ID NO: 3, SEQ ID NO: 4, SEQ ID NO: 5, or SEQ ID NO: 6;

f) an amino acid sequence differing from SEQ ID NO: 1, SEQ ID NO: 2, SEQ ID NO: 3, SEQ ID NO: 4, SEQ ID NO: 5, or SEQ ID NO: 6 by truncation at the N-terminus by at least one amino acid, such as between 1 and 10 amino acids, for example between 1 and 5 amino acids, or a variant thereof having between 1 and 10 amino acid substitutions and/or deletions as compared to SEQ ID NO: 1, SEQ ID NO: 2, SEQ ID NO: 3, SEQ ID NO: 4, SEQ ID NO: 5, or SEQ ID NO: 6; and g) an amino acid sequence differing from SEQ ID NO: 1, SEQ ID NO: 2, SEQ ID NO: 3, SEQ ID NO: 4, SEQ ID NO: 5, or SEQ ID NO: 6 by truncation at the C-terminus by at least one amino acid, such as between 1 and 10 amino acids, for example between 1 and 5 amino acids, or a variant thereof having between 1 and 10 amino acid substitutions and/or deletions as compared to SEQ ID NO: 1, SEQ ID NO: 2, SEQ ID NO: 3, SEQ ID NO: 4, SEQ ID NO: 5, or SEQ ID NO: 6.

In a specific embodiment, the method comprises the step of contacting a venom with a polypeptide comprising or consisting of a) the amino acid sequence as set forth in SEQ ID NO: 5;
b) a variant of SEQ ID NO: 5, wherein said variant has at least 80% sequence identity to SEQ ID NO: 5;
c) a variant of SEQ ID NO: 5, wherein said variant has between 1 and 10 amino acid substitutions and/or deletions as compared to SEQ ID NO: 5;
d) a fragment of SEQ ID NO: 5, or a variant thereof having between 1 and 10 amino acid substitutions and/or deletions as compared to SEQ ID NO: 5, such as between 1 and 5, for example between 1 and 3 amino acid substitutions and/or deletions as compared to SEQ ID NO: 5;
e) a fragment of SEQ ID NO: 5, or a variant thereof having between 3 and 18 consecutive amino acids of SEQ ID NO: 5, such as between 5 and 15, for example between 7 and 12 consecutive amino acids of SEQ ID NO: 5;
f) an amino acid sequence differing from SEQ ID NO: 5 by truncation at the N-terminus by at least one amino acid, such as between 1 and 10 amino acids, for example between 1 and 5 amino acids, or a variant thereof having between 1 and 10 amino acid substitutions and/or deletions as compared to SEQ ID NO: 5; and
g) an amino acid sequence differing from SEQ ID NO: 5 by truncation at the C-terminus by at least one amino acid, such as between 1 and 10 amino acids, for example between 1 and 5 amino acids, or a variant thereof having between 1 and 10 amino acid substitutions and/or deletions as compared to SEQ ID NO: 5.

Polypeptide Having Myotoxin-Neutralizing Properties

The present invention provides an isolated polypeptide having myotoxin-neutralizing activity. In one embodiment, the polypeptide is a non-natural polypeptide. The term 'non-natural polypeptide' as used herein, refers to a polypeptide having a random amino acid sequence which is not derived from any naturally occurring protein or fragments thereof, i.e. an amino acid sequence which is not isolated from any naturally occurring protein or fragments thereof. The polypeptides are derived from a naïve phage display library.

In one embodiment, the present invention provides a polypeptide having myotoxin-neutralizing activity.

In one embodiment, the myotoxin is a phospholipase $A_2$. The phospholipase $A_2$ may additionally be a nephrotoxin, a neurotoxin and/or a cytotoxin.

In one embodiment, the myotoxin is a phospholipase $A_2$ belonging to the group II PLA2s.

In one embodiment, the myotoxin is a phospholipase $A_2$ selected from the group consisting of Lys49 PLA2 homologue and Asp49 PLA2s.

In one embodiment, the myotoxin is a phospholipase $A_2$ which is a Lys49 PLA2 homologue.

In one embodiment, the myotoxin is myotoxin I and/or myotoxin II.

In one embodiment, the myotoxin is myotoxin II.

In some embodiments, the myotoxin is from a venom selected from the group consisting of snake venom, lizard venom, insect venom, jellyfish venom, scorpion venom and cone snail venom.

In one embodiment, the myotoxin is from a venom selected from the group consisting of snake venom, spider venom, scorpion venom and bee venom. Preferably, the myotoxin is from a snake venom.

The snake venom may be from any snake, the venom of which comprises myotoxin. In one embodiment, the venom is from a snake, such as from a viperidae, for example from a *Bothrops* species, an *Agkistrodon* species, a *Protobothrops* species, a *Lachesis* species such as *Lachesis muta muta*, a *Bitis* species such as *Bitis caudalis*, an *Atropoides* species such as *Atropoides nummifer mexicanus* or a *Trimeresurus* species; from a sea snake, for example from an *Aipsurus* species such as an *Aipsurus laevis*; or from a land elapid, for example from a *Micrurus* species such as *Micrurus nigrocinctus* or from a *Dendroaspis* species such as *Dendroaspis polyepis*. Preferably, the venom is from a *Bothrops* species, more preferably from *Bothrops asper*. In preferred embodiments, the venom is from a snake selected from the group consisting of *Bitis caudalis, Atropoides nummifer mexicanus, Apisurus laevis, Lachesis muta muta, Micrurus nigrocintus, Dendroaspis polyepis* or *Bothrops asper*, most preferably the venom is from *Bitis caudalis, Atropoides nummifer mexicanus, Lachesis muta muta, Dendroaspis polyepis* or *Bothrops asper*.

In one embodiment, the myotoxin is from a snake venom, such as from viperidae venom, for example from a *Bothrops* species, a *Agkistrodon* species, a *Protobothrops* species or a *Trimeresurus* species.

Preferably, the myotoxin is from a venom of a *Bothrops* species, more preferably from *Bothrops asper*, or any isoform thereof.

In one embodiment, the polypeptides as described herein have α-cobratoxin-neutralizing properties.

In some embodiments, the polypeptide is derived from SEQ ID NO: 5, as described in detail below. In other embodiments, the polypeptide is derived from SEQ ID NO: 1, SEQ ID NO: 2, SEQ ID NO: 3, SEQ ID NO: 4 or SEQ ID NO: 6 as described in detail herein below.

In one embodiment, the polypeptide comprises or consists of an amino acid sequence selected from the group consisting of a) the amino acid sequence according to SEQ ID NO: 5;
b) a variant of SEQ ID NO: 5, wherein said variant has at least 80% sequence identity to SEQ ID NO: 5;
c) a variant of SEQ ID NO: 5, wherein said variant has between 1 and 10 amino acid substitutions and/or deletions as compared to SEQ ID NO: 5;

d) a fragment of SEQ ID NO: 5, or a variant thereof having between 1 and 10 amino acid substitutions and/or deletions as compared to SEQ ID NO: 5, such as between 1 and 5, for example between 1 and 3 amino acid substitutions and/or deletions as compared to SEQ ID NO: 5;

e) a fragment of SEQ ID NO: 5, or a variant thereof having between 3 and 18 consecutive amino acids as compared to SEQ ID NO: 5, such as between 5 and 15, for example between 7 and 12 consecutive amino acids as compared to SEQ ID NO: 5;

f) an amino acid sequence differing from SEQ ID NO: 5 by truncation at the N-terminus by at least one amino acid, such as between 1 and 10 amino acids, for example between 1 and 5 amino acids, or a variant thereof having between 1 and 10 amino acid substitutions and/or deletions as compared to SEQ ID NO: 5; and g) an amino acid sequence differing from SEQ ID NO: 5 by truncation at the C-terminus by at least one amino acid, such as between 1 and 10 amino acids, for example between 1 and 5 amino acids, or a variant thereof having between 1 and 10 amino acid substitutions and/or deletions as compared to SEQ ID NO: 5.

In specific embodiments where the polypeptide comprises or consists of an amino acid sequence derived from SEQ ID NO: 5 as described above, the polypeptide preferably comprises one or more of:

the tryptophan residue at position 3 of SEQ ID NO: 5 (W3)

the tryptophan residue at position 5 of SEQ ID NO: 5 (W5)

the tyrosine residue at position 11 of SEQ ID NO: 5 (Y11).

In some embodiments where the polypeptide comprises or consists of an amino acid sequence derived from SEQ ID NO: 5 as described herein, the polypeptide comprises at least 15 amino acids of SEQ ID NO: 5, such as at least 16 amino acids of SEQ ID NO: 5, such as at least 17 amino acids of SEQ ID NO: 5, such as at least 18 amino acids of SEQ ID NO: 5, such as at least 19 amino acids of SEQ ID NO: 5, such as all 20 amino acids of SEQ ID NO: 5, which may be consecutive. Thus the sequence corresponding to the sequence of SEQ ID NO: 5 comprised in the polypeptide may be the 15 C-terminal amino acids of SEQ ID NO: 5, for example the 16 C-terminal amino acids of SEQ ID NO: 5, for example the 17 C-terminal amino acids of SEQ ID NO: 5, for example the 18 C-terminal amino acids of SEQ ID NO: 5, for example the 19 C-terminal amino acids of SEQ ID NO: 5, corresponding to, respectively, an N-terminal truncation of 1, 2, 3 or 4 amino acids of SEQ ID NO: 5. Similarly, the sequence corresponding to the sequence of SEQ ID NO: 5 comprised in the polypeptide may be the 15 N-terminal amino acids of SEQ ID NO: 5, for example the 16 N-terminal amino acids of SEQ ID NO: 5, for example the 17 N-terminal amino acids of SEQ ID NO: 5, for example the 18 N-terminal amino acids of SEQ ID NO: 5, for example the 19 N-terminal amino acids of SEQ ID NO: 5, corresponding to, respectively, a C-terminal truncation of 1, 2, 3 or 4 amino acids of SEQ ID NO: 5. In some embodiments, the truncated sequence corresponding to SEQ ID NO: 5 may be an N-terminal and a C-terminal truncation. For example, the sequence corresponding to SEQ ID NO: 5 may have a truncation of one C-terminal amino acid and 3 N-terminal amino acids, or a truncation of 2 C-terminal amino acids and 2 N-terminal amino acids, or a truncation of 3 C-terminal amino acids and one N-terminal amino acids, or a truncation of 4 C-terminal amino acids, or a truncation of 4 N-terminal amino acids, so that the total truncation is of at the most 4 amino acids compared to SEQ ID NO: 5.

In one embodiment, the polypeptide comprises or consists of the amino acid sequence DHWVWGWNYQYQPQEWHTES (SEQ ID NO: 5) or a fragment or variant thereof. Preferably, one, two or three of residues W3, W5 or Y11 are unmodified in variants of SEQ ID NO: 5.

Without being bound by theory, the data obtained by the inventors indicate that residues W3, W5 and Y11 are important for tertiary structure of the polypeptide, which in turn is important for its antitoxin activity. Accordingly, variants of SEQ ID NO: 5 are variants which preferably retain a tertiary structure similar to the structure of the polypeptide of SEQ ID NO: 5. The skilled person will know how to test whether the tertiary structure is maintained. For example this can be tested using fluorescence polarization binding assays, as described in example 10.

In some embodiments, the variant of SEQ ID NO: 5, has at least 80% sequence identity to SEQ ID NO: 5, for example at least 85% sequence identity to SEQ ID NO: 5, such as at least 90%, for example at least 95% sequence identity to SEQ ID NO: 5.

In some embodiments, the variant of SEQ ID NO: 5 has between 1 and 10 amino acid substitutions and/or deletions as compared to SEQ ID NO: 5, such as between 1 and 9, for example between 1 and 8, such as between 1 and 7, for example between 1 and 6, such as between 1 and 5, for example between 1 and 4, such as between 1 and 3, for example 2 amino acid substitutions/and or deletions as compared to SEQ ID NO: 5.

In some embodiments, the fragment of SEQ ID NO: 5, or a variant thereof has between 1 and 10 amino acid substitutions and/or deletions as compared to SEQ ID NO: 5, such as between 1 and 9, for example between 1 and 8, such as between 1 and 7, for example between 1 and 6, such as between 1 and 5, for example between 1 and 4, such as between 1 and 3, for example 2 amino acid substitutions/and or deletions as compared to SEQ ID NO: 5.

In some embodiments, the fragment of SEQ ID NO: 5, or a variant thereof has between 1 and 19 consecutive amino acids as compared to SEQ ID NO: 5, such as between 2 and 18, for example between 3 and 17, such as between 4 and 16, for example between 5 and 15, such as between 6 and 14, for example between 7 and 13, such as between 8 and 12, for example between 9 and 11, such as 10 consecutive amino acids as compared to SEQ ID NO: 5.

In some embodiments, the fragment of SEQ ID NO: 5, or a variant thereof has between 1 and 19 consecutive amino acids as compared to SEQ ID NO: 5, such as between 1 and 18, for example between 1 and 17, such as between 1 and 16, for example between 1 and 15, such as between 1 and 14, for example between 1 and 13, such as between 1 and 12, for example between 1 and 11, such as between 1 and 10, for example between 1 and 9, such as between 1 and 8, for example between 1 and 7, such as between 1 and 6, for example between 1 and 5 consecutive amino acids as compared to SEQ ID NO: 5.

In some embodiments, the fragment of SEQ ID NO: 5, or a variant thereof has between 1 and 19 consecutive amino acids as compared to SEQ ID NO: 5, such as between 2 and 19, for example between 3 and 19, such as between 4 and 19, for example between 5 and 19, such as between 6 and 19, for example between 7 and 19, such as between 8 and 19, for example between 9 and 19, such as between 10 and 19, for example between 11 and 19, such as between 12 and 19, for example between 13 and 19, such as between 14 and 19, for example between 15 and 19, such as between 16 and 19, for example between 17 and 19, such as between 18 and 19, for example 19 consecutive amino acids as compared to SEQ ID NO: 5.

In some embodiments, the fragment has an amino acid sequence differing from SEQ ID NO: 5 by truncation at the N-terminus by at least one amino acid, for example between 1 and 10 amino acids, such as between 1 and 9, for example between 1 and 8, such as between 1 and 7, for example between 1 and 6, such as between 1 and 5, for example between 1 and 4, such as between 1 and 3, for example 2 amino acids, or a variant thereof having between 1 and 10 amino acid substitutions and/or deletions as compared to SEQ ID NO: 5, such as between 1 and 9, for example between 1 and 8, such as between 1 and 7, for example between 1 and 6, such as between 1 and 5, for example between 1 and 4, such as between 1 and 3, for example 2 amino acid substitutions and/or deletions as compared to SEQ ID NO: 5.

In some embodiments, the fragment has an amino acid sequence differing from SEQ ID NO: 5 by truncation at the C-terminus by at least one amino acid, for example between 1 and 10 amino acids, such as between 1 and 9, for example between 1 and 8, such as between 1 and 7, for example between 1 and 6, such as between 1 and 5, for example between 1 and 4, such as between 1 and 3, for example 2 amino acids, or a variant thereof having between 1 and 10 amino acid substitutions and/or deletions as compared to SEQ ID NO: 5, such as between 1 and 9, for example between 1 and 8, such as between 1 and 7, for example between 1 and 6, such as between 1 and 5, for example between 1 and 4, such as between 1 and 3, for example 2 amino acid substitutions and/or deletions as compared to SEQ ID NO: 5.

Other polypeptides useful for the present methods may be derived from SEQ ID NO: 1, SEQ ID NO: 2, SEQ ID NO: 3, SEQ ID NO: 4 or SEQ ID NO: 6, as detailed below.

In one embodiment, the polypeptide comprises or consists of an amino acid sequence selected from the group consisting of
  a) the amino acid sequence according to SEQ ID NO: 1;
  b) a variant of SEQ ID NO: 1, wherein said variant has at least 80% sequence identity to SEQ ID NO: 1;
  c) a variant of SEQ ID NO: 1, wherein said variant has between 1 and 10 amino acid substitutions and/or deletions as compared to SEQ ID NO: 1;
  d) a fragment of SEQ ID NO: 1, or a variant thereof having between 1 and 10 amino acid substitutions and/or deletions as compared to SEQ ID NO: 1, such as between 1 and 5, for example between 1 and 3 amino acid substitutions and/or deletions as compared to SEQ ID NO: 1;
  e) a fragment of SEQ ID NO: 1, or a variant thereof having between 3 and 18 consecutive amino acids as compared to SEQ ID NO: 1, such as between 5 and 15, for example between 7 and 12 consecutive amino acids as compared to SEQ ID NO: 1;
  f) an amino acid sequence differing from SEQ ID NO: 1 by truncation at the N-terminus by at least one amino acid, such as between 1 and 10 amino acids, for example between 1 and 5 amino acids, or a variant thereof having between 1 and 10 amino acid substitutions and/or deletions as compared to SEQ ID NO: 1; and
  g) an amino acid sequence differing from SEQ ID NO: 1 by truncation at the C-terminus by at least one amino acid, such as between 1 and 10 amino acids, for example between 1 and 5 amino acids, or a variant thereof having between 1 and 10 amino acid substitutions and/or deletions as compared to SEQ ID NO: 1.

In one embodiment, the polypeptide comprises or consists of an amino acid sequence selected from the group consisting of
  a) the amino acid sequence according to SEQ ID NO: 2;
  b) a variant of SEQ ID NO: 2, wherein said variant has at least 80% sequence identity to SEQ ID NO: 2;
  c) a variant of SEQ ID NO: 2, wherein said variant has between 1 and 10 amino acid substitutions and/or deletions as compared to SEQ ID NO: 2;
  d) a fragment of SEQ ID NO: 2, or a variant thereof having between 1 and 10 amino acid substitutions and/or deletions as compared to SEQ ID NO: 2, such as between 1 and 5, for example between 1 and 3 amino acid substitutions and/or deletions as compared to SEQ ID NO: 2;
  e) a fragment of SEQ ID NO: 2, or a variant thereof having between 3 and 18 consecutive amino acids as compared to SEQ ID NO: 2, such as between 5 and 15, for example between 7 and 12 consecutive amino acids as compared to SEQ ID NO: 2;
  f) an amino acid sequence differing from SEQ ID NO: 2 by truncation at the N-terminus by at least one amino acid, such as between 1 and 10 amino acids, for example between 1 and 5 amino acids, or a variant thereof having between 1 and 10 amino acid substitutions and/or deletions as compared to SEQ ID NO: 2; and
  g) an amino acid sequence differing from SEQ ID NO: 2 by truncation at the C-terminus by at least one amino acid, such as between 1 and 10 amino acids, for example between 1 and 5 amino acids, or a variant thereof having between 1 and 10 amino acid substitutions and/or deletions as compared to SEQ ID NO: 2.

In one embodiment, the polypeptide comprises or consists of an amino acid sequence selected from the group consisting of
  a) the amino acid sequence according to SEQ ID NO: 3;
  b) a variant of SEQ ID NO: 3, wherein said variant has at least 80% sequence identity to SEQ ID NO: 3;
  c) a variant of SEQ ID NO: 3, wherein said variant has between 1 and 10 amino acid substitutions and/or deletions as compared to SEQ ID NO: 3;
  d) a fragment of SEQ ID NO: 3, or a variant thereof having between 1 and 10 amino acid substitutions and/or deletions as compared to SEQ ID NO: 3, such as between 1 and 5, for example between 1 and 3 amino acid substitutions and/or deletions as compared to SEQ ID NO: 3;
  e) a fragment of SEQ ID NO: 3, or a variant thereof having between 3 and 18 consecutive amino acids as compared to SEQ ID NO: 3, such as between 5 and 15, for example between 7 and 12 consecutive amino acids as compared to SEQ ID NO: 3;
  f) an amino acid sequence differing from SEQ ID NO: 3 by truncation at the N-terminus by at least one amino acid, such as between 1 and 10 amino acids, for example between 1 and 5 amino acids, or a variant thereof having between 1 and 10 amino acid substitutions and/or deletions as compared to SEQ ID NO: 3; and
  g) an amino acid sequence differing from SEQ ID NO: 3 by truncation at the C-terminus by at least one amino acid, such as between 1 and 10 amino acids, for example between 1 and 5 amino acids, or a variant thereof having between 1 and 10 amino acid substitutions and/or deletions as compared to SEQ ID NO: 3.

In one embodiment, the polypeptide comprises or consists of an amino acid sequence selected from the group consisting of
  a) the amino acid sequence according to SEQ ID NO: 4;
  b) a variant of SEQ ID NO: 4, wherein said variant has at least 80% sequence identity to SEQ ID NO: 4;
  c) a variant of SEQ ID NO: 4, wherein said variant has between 1 and 10 amino acid substitutions and/or deletions as compared to SEQ ID NO: 4;
  d) a fragment of SEQ ID NO: 4, or a variant thereof having between 1 and 10 amino acid substitutions and/or deletions as compared to SEQ ID NO: 4, such as between 1 and 5, for example between 1 and 3 amino acid substitutions and/or deletions as compared to SEQ ID NO: 4;
  e) a fragment of SEQ ID NO: 4, or a variant thereof having between 3 and 18 consecutive amino acids as compared to SEQ ID NO: 4, such as between 5 and 15, for example between 7 and 12 consecutive amino acids as compared to SEQ ID NO: 4;
  f) an amino acid sequence differing from SEQ ID NO: 4 by truncation at the N-terminus by at least one amino acid, such as between 1 and 10 amino acids, for example between 1 and 5 amino acids, or a variant thereof having between 1 and 10 amino acid substitutions and/or deletions as compared to SEQ ID NO: 4; and
  g) an amino acid sequence differing from SEQ ID NO: 4 by truncation at the C-terminus by at least one amino acid, such as between 1 and 10 amino acids, for example between 1 and 5 amino acids, or a variant thereof having between 1 and 10 amino acid substitutions and/or deletions as compared to SEQ ID NO: 4.

In one embodiment, the polypeptide comprises or consists of an amino acid sequence selected from the group consisting of
  a) the amino acid sequence according to SEQ ID NO: 6;
  b) a variant of SEQ ID NO: 6, wherein said variant has at least 80% sequence identity to SEQ ID NO: 6;
  c) a variant of SEQ ID NO: 6, wherein said variant has between 1 and 10 amino acid substitutions and/or deletions as compared to SEQ ID NO: 6;
  d) a fragment of SEQ ID NO: 6, or a variant thereof having between 1 and 10 amino acid substitutions and/or deletions as compared to SEQ ID NO: 6, such as between 1 and 5, for example between 1 and 3 amino acid substitutions and/or deletions as compared to SEQ ID NO: 6;
  e) a fragment of SEQ ID NO: 6, or a variant thereof having between 3 and 18 consecutive amino acids as compared to SEQ ID NO: 6, such as between 5 and 15, for example between 7 and 12 consecutive amino acids as compared to SEQ ID NO: 6;
  f) an amino acid sequence differing from SEQ ID NO: 6 by truncation at the N-terminus by at least one amino acid, such as between 1 and 10 amino acids, for example between 1 and 5 amino acids, or a variant thereof having between 1 and 10 amino acid substitutions and/or deletions as compared to SEQ ID NO: 6; and
  g) an amino acid sequence differing from SEQ ID NO: 6 by truncation at the C-terminus by at least one amino acid, such as between 1 and 10 amino acids, for example between 1 and 5 amino acids, or a variant thereof having between 1 and 10 amino acid substitutions and/or deletions as compared to SEQ ID NO: 6.

In one embodiment, the polypeptide comprises or consists of the amino acid sequence VNRMLELKIMDYGGG (SEQ ID NO: 1) or a fragment or variant thereof.

In one embodiment, the polypeptide comprises or consists of the amino acid sequence QSVTMGPGLITHSPIHTQSK (SEQ ID NO: 2) or a fragment or variant thereof.

In one embodiment, the polypeptide comprises or consists of the amino acid sequence DYDRIPDIPMLGGGG (SEQ ID NO: 3) or a fragment or variant thereof.

In one embodiment, the polypeptide comprises or consists of the amino acid sequence SWEPYANPTRYKFHDW (SEQ ID NO: 4) or a fragment or variant thereof.

In one embodiment, the polypeptide comprises or consists of the amino acid sequence NGYWSSQQYMQQAPMPWRIP (SEQ ID NO: 6) or a fragment or variant thereof.

Amino acids are named herein using either their 1-letter or 3-letter code according to the recommendations from IUPAC.

In some embodiments, the variant of SEQ ID NO: 1, has at least 73% sequence identity to SEQ ID NO: 1, for example at least 80% sequence identity to SEQ ID NO: 1, such as at least 86%, for example at least 93% sequence identity to SEQ ID NO: 1.

In some embodiments, the variant of SEQ ID NO: 2, has at least 80% sequence identity to SEQ ID NO: 2, for example at least 85% sequence identity to SEQ ID NO: 2, such as at least 90%, for example at least 95% sequence identity to SEQ ID NO: 2.

In some embodiments, the variant of SEQ ID NO: 3, has at least 73% sequence identity to SEQ ID NO: 3, for example at least 80% sequence identity to SEQ ID NO: 3, such as at least 86%, for example at least 93% sequence identity to SEQ ID NO: 3.

In some embodiments, the variant of SEQ ID NO: 4, has at least 75% sequence identity to SEQ ID NO: 4, for example at least 81% sequence identity to SEQ ID NO: 4, such as at least 87%, for example at least 93% sequence identity to SEQ ID NO: 4.

In some embodiments, the variant of SEQ ID NO: 6, has at least 80% sequence identity to SEQ ID NO: 6, for example at least 85% sequence identity to SEQ ID NO: 6, such as at least 90%, for example at least 95% sequence identity to SEQ ID NO: 6.

In some embodiments, the variant of SEQ ID NO: 1 has between 1 and 10 amino acid substitutions and/or deletions as compared to SEQ ID NO: 1, such as between 1 and 9, for example between 1 and 8, such as between 1 and 7, for example between 1 and 6, such as between 1 and 5, for example between 1 and 4, such as between 1 and 3, for example 2 amino acid substitutions/and or deletions as compared to SEQ ID NO: 1.

In some embodiments, the variant of SEQ ID NO: 2 has between 1 and 10 amino acid substitutions and/or deletions as compared to SEQ ID NO: 2, such as between 1 and 9, for example between 1 and 8, such as between 1 and 7, for example between 1 and 6, such as between 1 and 5, for example between 1 and 4, such as between 1 and 3, for example 2 amino acid substitutions/and or deletions as compared to SEQ ID NO: 2.

In some embodiments, the variant of SEQ ID NO: 3 has between 1 and 10 amino acid substitutions and/or deletions as compared to SEQ ID NO: 3, such as between 1 and 9, for example between 1 and 8, such as between 1 and 7, for example between 1 and 6, such as between 1 and 5, for example between 1 and 4, such as between 1 and 3, for example 2 amino acid substitutions/and or deletions as compared to SEQ ID NO: 3.

In some embodiments, the variant of SEQ ID NO: 4 has between 1 and 10 amino acid substitutions and/or deletions as compared to SEQ ID NO: 4, such as between 1 and 9, for example between 1 and 8, such as between 1 and 7, for example between 1 and 6, such as between 1 and 5, for example between 1 and 4, such as between 1 and 3, for example 2 amino acid substitutions/and or deletions as compared to SEQ ID NO: 4.

In some embodiments, the variant of SEQ ID NO: 6 has between 1 and 10 amino acid substitutions and/or deletions as compared to SEQ ID NO: 6, such as between 1 and 9, for example between 1 and 8, such as between 1 and 7, for example between 1 and 6, such as between 1 and 5, for example between 1 and 4, such as between 1 and 3, for example 2 amino acid substitutions/and or deletions as compared to SEQ ID NO: 6.

In some embodiments, the fragment of SEQ ID NO: 1, or a variant thereof has between 1 and 10 amino acid substitutions and/or deletions as compared to SEQ ID NO: 1, such as between 1 and 9, for example between 1 and 8, such as between 1 and 7, for example between 1 and 6, such as between 1 and 5, for example between 1 and 4, such as between 1 and 3, for example 2 amino acid substitutions/and or deletions as compared to SEQ ID NO: 1.

In some embodiments, the fragment of SEQ ID NO: 2, or a variant thereof has between 1 and 10 amino acid substitutions and/or deletions as compared to SEQ ID NO: 2, such as between 1 and 9, for example between 1 and 8, such as between 1 and 7, for example between 1 and 6, such as between 1 and 5, for example between 1 and 4, such as between 1 and 3, for example 2 amino acid substitutions/and or deletions as compared to SEQ ID NO: 2.

In some embodiments, the fragment of SEQ ID NO: 3, or a variant thereof has between 1 and 10 amino acid substitutions and/or deletions as compared to SEQ ID NO: 3, such as between 1 and 9, for example between 1 and 8, such as between 1 and 7, for example between 1 and 6, such as between 1 and 5, for example between 1 and 4, such as between 1 and 3, for example 2 amino acid substitutions/and or deletions as compared to SEQ ID NO: 3.

In some embodiments, the fragment of SEQ ID NO: 4, or a variant thereof has between 1 and 10 amino acid substitutions and/or deletions as compared to SEQ ID NO: 4, such as between 1 and 9, for example between 1 and 8, such as between 1 and 7, for example between 1 and 6, such as between 1 and 5, for example between 1 and 4, such as between 1 and 3, for example 2 amino acid substitutions/and or deletions as compared to SEQ ID NO: 4.

In some embodiments, the fragment of SEQ ID NO: 6, or a variant thereof has between 1 and 10 amino acid substitutions and/or deletions as compared to SEQ ID NO: 6, such as between 1 and 9, for example between 1 and 8, such as between 1 and 7, for example between 1 and 6, such as between 1 and 5, for example between 1 and 4, such as between 1 and 3, for example 2 amino acid substitutions/and or deletions as compared to SEQ ID NO: 6.

In some embodiments, the fragment of SEQ ID NO: 1, or a variant thereof has between 1 and 14 consecutive amino acids as compared to SEQ ID NO: 1, such as between 2 and 13, for example between 3 and 12, such as between 4 and 11, for example between 5 and 10, such as between 6 and 9, for example between 7 and 8 consecutive amino acids as compared to SEQ ID NO: 1.

In some embodiments, the fragment of SEQ ID NO: 1, or a variant thereof has between 1 and 14 consecutive amino acids as compared to SEQ ID NO: 1, such as between 1 and 13, for example between 1 and 12, such as between 1 and 11, for example between 1 and 10, such as between 1 and 9, for example between 1 and 8, such as between 1 and 7, for example between 1 and 6, such as between 1 and 5 consecutive amino acids as compared to SEQ ID NO: 1.

In some embodiments, the fragment of SEQ ID NO: 1, or a variant thereof has between 1 and 14 consecutive amino acids as compared to SEQ ID NO: 1, such as between 2 and 14, for example between 3 and 14, such as between 4 and 14, for example between 5 and 14, such as between 6 and 14, for example between 7 and 14, such as between 8 and 14, for example between 9 and 14, such as between 10 and 14, for example between 11 and 14, such as between 12 and 14, for example 14 consecutive amino acids as compared to SEQ ID NO: 1.

In some embodiments, the fragment of SEQ ID NO: 2, or a variant thereof has between 1 and 19 consecutive amino acids as compared to SEQ ID NO: 2, such as between 2 and 18, for example between 3 and 17, such as between 4 and 16, for example between 5 and 15, such as between 6 and 14, for example between 7 and 13, such as between 8 and 12, for example between 9 and 11, such as 10 consecutive amino acids as compared to SEQ ID NO: 2.

In some embodiments, the fragment of SEQ ID NO: 2, or a variant thereof has between 1 and 19 consecutive amino acids as compared to SEQ ID NO: 2, such as between 1 and 18, for example between 1 and 17, such as between 1 and 16, for example between 1 and 15, such as between 1 and 14, for example between 1 and 13, such as between 1 and 12, for example between 1 and 11, such as between 1 and 10, for example between 1 and 9, such as between 1 and 8, for example between 1 and 7, such as between 1 and 6, for example between 1 and 5 consecutive amino acids as compared to SEQ ID NO: 2.

In some embodiments, the fragment of SEQ ID NO: 2, or a variant thereof has between 1 and 19 consecutive amino acids as compared to SEQ ID NO: 2, such as between 2 and 19, for example between 3 and 19, such as between 4 and 19, for example between 5 and 19, such as between 6 and 19, for example between 7 and 19, such as between 8 and 19, for example between 9 and 19, such as between 10 and 19, for example between 11 and 19, such as between 12 and 19, for example between 13 and 19, such as between 14 and 19, for example between 15 and 19, such as between 16 and 19, for example between 17 and 19, such as between 18 and 19, for example 19 consecutive amino acids as compared to SEQ ID NO: 2.

In some embodiments, the fragment of SEQ ID NO: 3, or a variant thereof has between 1 and 14 consecutive amino acids as compared to SEQ ID NO: 3, such as between 2 and 13, for example between 3 and 12, such as between 4 and 11, for example between 5 and 10, such as between 6 and 9, for example between 7 and 8 consecutive amino acids as compared to SEQ ID NO: 3.

In some embodiments, the fragment of SEQ ID NO: 3, or a variant thereof has between 1 and 14 consecutive amino acids as compared to SEQ ID NO: 3, such as between 1 and 13, for example between 1 and 12, such as between 1 and 11, for example between 1 and 10, such as between 1 and 9, for example between 1 and 8, such as between 1 and 7, for example between 1 and 6, such as between 1 and 5 consecutive amino acids as compared to SEQ ID NO: 3.

In some embodiments, the fragment of SEQ ID NO: 3, or a variant thereof has between 1 and 14 consecutive amino acids as compared to SEQ ID NO: 3, such as between 2 and 14, for example between 3 and 14, such as between 4 and 14, for example between 5 and 14, such as between 6 and 14, for example between 7 and 14, such as between 8 and 14, for example between 9 and 14, such as between 10 and 14, for example between 11 and 14, such as between 12 and 14, for example 14 consecutive amino acids as compared to SEQ ID NO: 3.

In some embodiments, the fragment of SEQ ID NO: 4, or a variant thereof has between 1 and 15 consecutive amino acids as compared to SEQ ID NO: 4, such as between 2 and 14, for example between 3 and 13, such as between 4 and 12, for example between 5 and 11, such as between 6 and 10, for example between 7 and 9, such as 8 consecutive amino acids as compared to SEQ ID NO: 4.

In some embodiments, the fragment of SEQ ID NO: 4, or a variant thereof has between 1 and 15 consecutive amino acids as compared to SEQ ID NO: 4, such as between 1 and 14, for example between 1 and 13, such as between 1 and 12, for example between 1 and 11, such as between 1 and 10, for example between 1 and 9, such as between 1 and 8, for example between 1 and 7, such as between 1 and 6, for example between 1 and 5 consecutive amino acids as compared to SEQ ID NO: 4.

In some embodiments, the fragment of SEQ ID NO: 4, or a variant thereof has between 1 and 15 consecutive amino acids as compared to SEQ ID NO: 4, such as between 2 and 15, for example between 3 and 15, such as between 4 and 15, for example between 5 and 15, such as between 6 and 15, for example between 7 and 15, such as between 8 and 15, for example between 9 and 15, such as between 10 and 15, for example between 11 and 15, such as between 12 and 15, for example between 13 and 15, such as 14 consecutive amino acids as compared to SEQ ID NO: 4.

In some embodiments, the fragment of SEQ ID NO: 6, or a variant thereof has between 1 and 19 consecutive amino acids as compared to SEQ ID NO: 6, such as between 2 and 18, for example between 3 and 17, such as between 4 and 16, for example between 5 and 15, such as between 6 and 14, for example between 7 and 13, such as between 8 and 12, for example between 9 and 11, such as 10 consecutive amino acids as compared to SEQ ID NO: 6.

In some embodiments, the fragment of SEQ ID NO: 6, or a variant thereof has between 1 and 19 consecutive amino acids as compared to SEQ ID NO: 6, such as between 1 and 18, for example between 1 and 17, such as between 1 and 16, for example between 1 and 15, such as between 1 and 14, for example between 1 and 13, such as between 1 and 12, for example between 1 and 11, such as between 1 and 10, for example between 1 and 9, such as between 1 and 8, for example between 1 and 7, such as between 1 and 6, for example between 1 and 5 consecutive amino acids as compared to SEQ ID NO: 6.

In some embodiments, the fragment of SEQ ID NO: 6, or a variant thereof has between 1 and 19 consecutive amino acids as compared to SEQ ID NO: 6, such as between 2 and 19, for example between 3 and 19, such as between 4 and 19, for example between 5 and 19, such as between 6 and 19, for example between 7 and 19, such as between 8 and 19, for example between 9 and 19, such as between 10 and 19, for example between 11 and 19, such as between 12 and 19, for example between 13 and 19, such as between 14 and 19, for example between 15 and 19, such as between 16 and 19, for example between 17 and 19, such as between 18 and 19, for example 19 consecutive amino acids as compared to SEQ ID NO: 6.

In some embodiments, the fragment has an amino acid sequence differing from SEQ ID NO: 1 by truncation at the N-terminus by at least one amino acid, for example between 1 and 10 amino acids, such as between 1 and 9, for example between 1 and 8, such as between 1 and 7, for example between 1 and 6, such as between 1 and 5, for example between 1 and 4, such as between 1 and 3, for example 2 amino acids, or a variant thereof having between 1 and 10 amino acid substitutions and/or deletions as compared to SEQ ID NO: 1, such as between 1 and 9, for example between 1 and 8, such as between 1 and 7, for example between 1 and 6, such as between 1 and 5, for example between 1 and 4, such as between 1 and 3, for example 2 amino acid substitutions and/or deletions as compared to SEQ ID NO: 1.

In some embodiments, the fragment has an amino acid sequence differing from SEQ ID NO: 2 by truncation at the N-terminus by at least one amino acid, for example between 1 and 10 amino acids, such as between 1 and 9, for example between 1 and 8, such as between 1 and 7, for example between 1 and 6, such as between 1 and 5, for example between 1 and 4, such as between 1 and 3, for example 2 amino acids, or a variant thereof having between 1 and 10 amino acid substitutions and/or deletions as compared to SEQ ID NO: 2, such as between 1 and 9, for example between 1 and 8, such as between 1 and 7, for example between 1 and 6, such as between 1 and 5, for example between 1 and 4, such as between 1 and 3, for example 2 amino acid substitutions and/or deletions as compared to SEQ ID NO: 2.

In some embodiments, the fragment has an amino acid sequence differing from SEQ ID NO: 3 by truncation at the N-terminus by at least one amino acid, for example between 1 and 10 amino acids, such as between 1 and 9, for example between 1 and 8, such as between 1 and 7, for example between 1 and 6, such as between 1 and 5, for example between 1 and 4, such as between 1 and 3, for example 2 amino acids, or a variant thereof having between 1 and 10 amino acid substitutions and/or deletions as compared to SEQ ID NO: 3, such as between 1 and 9, for example between 1 and 8, such as between 1 and 7, for example between 1 and 6, such as between 1 and 5, for example between 1 and 4, such as between 1 and 3, for example 2 amino acid substitutions and/or deletions as compared to SEQ ID NO: 3.

In some embodiments, the fragment has an amino acid sequence differing from SEQ ID NO: 4 by truncation at the N-terminus by at least one amino acid, for example between 1 and 10 amino acids, such as between 1 and 9, for example between 1 and 8, such as between 1 and 7, for example between 1 and 6, such as between 1 and 5, for example between 1 and 4, such as between 1 and 3, for example 2 amino acids, or a variant thereof having between 1 and 10 amino acid substitutions and/or deletions as compared to SEQ ID NO: 4, such as between 1 and 9, for example between 1 and 8, such as between 1 and 7, for example between 1 and 6, such as between 1 and 5, for example between 1 and 4, such as between 1 and 3, for example 2 amino acid substitutions and/or deletions as compared to SEQ ID NO: 4.

In some embodiments, the fragment has an amino acid sequence differing from SEQ ID NO: 6 by truncation at the N-terminus by at least one amino acid, for example between 1 and 10 amino acids, such as between 1 and 9, for example between 1 and 8, such as between 1 and 7, for example between 1 and 6, such as between 1 and 5, for example between 1 and 4, such as between 1 and 3, for example 2 amino acids, or a variant thereof having between 1 and 10 amino acid substitutions and/or deletions as compared to SEQ ID NO: 6, such as between 1 and 9, for example between 1 and 8, such as between 1 and 7, for example between 1 and 6, such as between 1 and 5, for example between 1 and 4, such as between 1 and 3, for example 2 amino acid substitutions and/or deletions as compared to SEQ ID NO: 6.

In some embodiments, the fragment has an amino acid sequence differing from SEQ ID NO: 1 by truncation at the C-terminus by at least one amino acid, for example between 1 and 10 amino acids, such as between 1 and 9, for example between 1 and 8, such as between 1 and 7, for example between 1 and 6, such as between 1 and 5, for example between 1 and 4, such as between 1 and 3, for example 2 amino acids, or a variant thereof having between 1 and 10 amino acid substitutions and/or deletions as compared to SEQ ID NO: 1, such as between 1 and 9, for example between 1 and 8, such as between 1 and 7, for example between 1 and 6, such as between 1 and 5, for example between 1 and 4, such as between 1 and 3, for example 2 amino acid substitutions and/or deletions as compared to SEQ ID NO: 1.

In some embodiments, the fragment has an amino acid sequence differing from SEQ ID NO: 2 by truncation at the C-terminus by at least one amino acid, for example between 1 and 10 amino acids, such as between 1 and 9, for example between 1 and 8, such as between 1 and 7, for example between 1 and 6, such as between 1 and 5, for example between 1 and 4, such as between 1 and 3, for example 2 amino acids, or a variant thereof having between 1 and 10 amino acid substitutions and/or deletions as compared to SEQ ID NO: 2, such as between 1 and 9, for example between 1 and 8, such as between 1 and 7, for example between 1 and 6, such as between 1 and 5, for example between 1 and 4, such as between 1 and 3, for example 2 amino acid substitutions and/or deletions as compared to SEQ ID NO: 2.

In some embodiments, the fragment has an amino acid sequence differing from SEQ ID NO: 3 by truncation at the C-terminus by at least one amino acid, for example between 1 and 10 amino acids, such as between 1 and 9, for example between 1 and 8, such as between 1 and 7, for example between 1 and 6, such as between 1 and 5, for example between 1 and 4, such as between 1 and 3, for example 2 amino acids, or a variant thereof having between 1 and 10 amino acid substitutions and/or deletions as compared to SEQ ID NO: 3, such as between 1 and 9, for example between 1 and 8, such as between 1 and 7, for example between 1 and 6, such as between 1 and 5, for example between 1 and 4, such as between 1 and 3, for example 2 amino acid substitutions and/or deletions as compared to SEQ ID NO: 3.

In some embodiments, the fragment has an amino acid sequence differing from SEQ ID NO: 4 by truncation at the C-terminus by at least one amino acid, for example between 1 and 10 amino acids, such as between 1 and 9, for example between 1 and 8, such as between 1 and 7, for example between 1 and 6, such as between 1 and 5, for example between 1 and 4, such as between 1 and 3, for example 2 amino acids, or a variant thereof having between 1 and 10 amino acid substitutions and/or deletions as compared to SEQ ID NO: 4, such as between 1 and 9, for example between 1 and 8, such as between 1 and 7, for example between 1 and 6, such as between 1 and 5, for example between 1 and 4, such as between 1 and 3, for example 2 amino acid substitutions and/or deletions as compared to SEQ ID NO: 4.

In some embodiments, the fragment has an amino acid sequence differing from SEQ ID NO: 6 by truncation at the C-terminus by at least one amino acid, for example between 1 and 10 amino acids, such as between 1 and 9, for example between 1 and 8, such as between 1 and 7, for example between 1 and 6, such as between 1 and 5, for example between 1 and 4, such as between 1 and 3, for example 2 amino acids, or a variant thereof having between 1 and 10 amino acid substitutions and/or deletions as compared to SEQ ID NO: 6, such as between 1 and 9, for example between 1 and 8, such as between 1 and 7, for example between 1 and 6, such as between 1 and 5, for example between 1 and 4, such as between 1 and 3, for example 2 amino acid substitutions and/or deletions as compared to SEQ ID NO: 6.

In one embodiment, the amino acid substitutions are conservative substitutions.

The variant or fragment may be any variant or fragment described herein above.

In some embodiments, the polypeptide as described herein, comprising or consisting of SEQ ID NO: 1, 2, 3, 4, 5 or 6 or a variant or fragment thereof as described herein, has a length of less than 100, 95, 90, 85, 80, 75, 70, 65, 60, 55, 50, 45, 40, 35, 30, 25, 20, 15, 10 or 5 amino acids.

In some embodiments, the polypeptide as described herein, comprising or consisting of SEQ ID NO: 1, 2, 3, 4, 5 or 6 or a variant or fragment thereof as described herein, has a length of less than 25, 24, 23, 22, 21, 20, 19, 18, 17, 16 or 15 amino acids.

In some embodiments, the polypeptide as described herein, comprising or consisting of SEQ ID NO: 1, 2, 3, 4, 5 or 6 or a variant or fragment thereof as described herein, has a length of at least 5, 10, 15, 20, 25, 30, 35, 40, 45, 50, 55, 60, 65, 70, 75, 80, 85, 90, 95 or 100 amino acids.

In some embodiments, the polypeptide as described herein, comprising or consisting of SEQ ID NO: 1, 2, 3, 4, 5 or 6 or a variant or fragment thereof as described herein, has a length of at least 15, 16, 17, 18, 19, 20, 21, 22, 23, 24 or 25 amino acids.

The polypeptide may be modified as to improve the pharmacokinetic properties of said polypeptide. Such modification may be beneficial in order to improve for example proteolytic stability, plasma half-life and distribution. In particular, polypeptides derived from SEQ ID NO: 5 as described herein may be further modified.

Thus, in one embodiment, the polypeptide comprises one or more non-natural amino acid(s). The term 'non-natural amino acid' as used herein, also known as non-coded or non-proteinogenic amino acids, refers to non-canonical amino acids which are not encoded by the transcriptome. Examples of non-natural amino acids include but are not limited to hydroxyproline, 2-aminoisobutyric acid, naphthylalanine and diaminopropionic acid.

In one embodiment, the polypeptide comprises one or more D-amino acid(s).

In one embodiment, the polypeptide is a peptoid.

In one embodiment, the polypeptide is alkylated at one or more backbone amide nitrogen(s).

In one embodiment, the polypeptide is acetylated at the N-terminus.

In one embodiment, the polypeptide comprises a C-terminal amide.

In one embodiment, the polypeptide has been cyclized. Examples of potential cyclizations include but are not limited to stapling of the polypeptide, cyclotides, amide bond cyclization, thioether cyclization, CLIPS cyclization and Cys-Cys cyclization.

In one embodiment, the polypeptide is modified by a post translational modification, such as for example modified by phosphorylation, methylation or acylation.

In some embodiments, the polypeptide is modified by PEGylation and/or biotinylation as is known in the art.

The polypeptides as described herein may be prepared by any means generally known in the art for peptide preparation. Such method may for example be synthesis via solution phase synthesis or solid phase peptide synthesis. The polypeptides may alternatively be prepared by heterologous expression in a suitable host cell, as is known in the art.

In one embodiment, the polypeptide further comprises one or more moieties conjugated to said polypeptide. Said one or more moieties may be selected from the group consisting of albumin, an albumin binding moiety, biotin, fatty acids, polyethylene glycol (PEG), acylation groups, proteins, peptides, nanobodies, antibodies and antibody fragments.

In one embodiment, the polypeptide and said one or more moieties are conjugated to each other by a linker. The term 'linker' as used herein, refers to a molecular moiety which is capable of binding two molecules to one another. The linker may be of varying length and structure. The linker may be a non-degradable linkage or a linkage containing an intracellularly degradable bond, e.g. a disulphide bond. Potentially, the degradable linker is designed as a self-immolative linker (SIL) capable of releasing the native polypeptide upon degradation.

In one embodiment, the polypeptide has been immobilized on a solid support. Immobilization of the polypeptides on a solid support may provide means for affinity purification or for pull-down experiments of said myotoxins, or for providing a patch comprising the polypeptide or other devices useful in the context of treating envenomation.

In one embodiment, the present invention provides a polynucleotide encoding the polypeptide as described herein. The polynucleotide may be codon optimized. In particular, are disclosed herein a polynucleotide encoding a polypeptide comprising or consisting of an amino acid sequence selected from the group consisting of
  a) the amino acid sequence according to SEQ ID NO: 1, SEQ ID NO: 2, SEQ ID NO: 3, SEQ ID NO: 4, SEQ ID NO: 5, or SEQ ID NO: 6;
  b) a variant of SEQ ID NO: 1, SEQ ID NO: 2, SEQ ID NO: 3, SEQ ID NO: 4, SEQ ID NO: 5, or SEQ ID NO: 6, wherein said variant has at least 80% sequence identity to SEQ ID NO: 1, SEQ ID NO: 2, SEQ ID NO: 3, SEQ ID NO: 4, SEQ ID NO: 5, or SEQ ID NO: 6;
  c) a variant of SEQ ID NO: 1, SEQ ID NO: 2, SEQ ID NO: 3, SEQ ID NO: 4, SEQ ID NO: 5, or SEQ ID NO: 6, wherein said variant has between 1 and 10 amino acid substitutions and/or deletions as compared to SEQ ID NO: 1, SEQ ID NO: 2, SEQ ID NO: 3, SEQ ID NO: 4, SEQ ID NO: 5, or SEQ ID NO: 6;
  d) a fragment of SEQ ID NO: 1, SEQ ID NO: 2, SEQ ID NO: 3, SEQ ID NO: 4, SEQ ID NO: 5, or SEQ ID NO: 6, or a variant thereof having between 1 and 10 amino acid substitutions and/or deletions as compared to SEQ ID NO: 1, SEQ ID NO: 2, SEQ ID NO: 3, SEQ ID NO: 4, SEQ ID NO: 5, or SEQ ID NO: 6, such as between 1 and 5, for example between 1 and 3 amino acid substitutions and/or deletions as compared to SEQ ID NO: 1, SEQ ID NO: 2, SEQ ID NO: 3, SEQ ID NO: 4, SEQ ID NO: 5, or SEQ ID NO: 6;
  e) a fragment of SEQ ID NO: 1, SEQ ID NO: 2, SEQ ID NO: 3, SEQ ID NO: 4, SEQ ID NO: 5, or SEQ ID NO: 6, or a variant thereof having between 3 and 18 consecutive amino acids as compared to SEQ ID NO: 1, SEQ ID NO: 2, SEQ ID NO: 3, SEQ ID NO: 4, SEQ ID NO: 5, or SEQ ID NO: 6, such as between 5 and 15, for example between 7 and 12 consecutive amino acids as compared to SEQ ID NO: 1, SEQ ID NO: 2, SEQ ID NO: 3, SEQ ID NO: 4, SEQ ID NO: 5, or SEQ ID NO: 6;
  f) an amino acid sequence differing from SEQ ID NO: 1, SEQ ID NO: 2, SEQ ID NO: 3, SEQ ID NO: 4, SEQ ID NO: 5, or SEQ ID NO: 6 by truncation at the N-terminus by at least one amino acid, such as between 1 and 10 amino acids, for example between 1 and 5 amino acids, or a variant thereof having between 1 and 10 amino acid substitutions and/or deletions as compared to SEQ ID NO: 1, SEQ ID NO: 2, SEQ ID NO: 3, SEQ ID NO: 4, SEQ ID NO: 5, or SEQ ID NO: 6; and
  g) an amino acid sequence differing from SEQ ID NO: 1, SEQ ID NO: 2, SEQ ID NO: 3, SEQ ID NO: 4, SEQ ID NO: 5, or SEQ ID NO: 6 by truncation at the C-terminus by at least one amino acid, such as between 1 and 10 amino acids, for example between 1 and 5 amino acids, or a variant thereof having between 1 and 10 amino acid substitutions and/or deletions as compared to SEQ ID NO: 1, SEQ ID NO: 2, SEQ ID NO: 3, SEQ ID NO: 4, SEQ ID NO: 5, or SEQ ID NO: 6

In particular embodiments, the polynucleotide encodes a polypeptide derived from SEQ ID NO: 5 as described herein.

In one embodiment, the present invention provides a vector comprising the polynucleotide encoding the polypeptide as described herein. The vector may be any vector, such as for example a plasmid vector, a viral vector or an expression vector. The vector may comprise a promoter that drives expression of the transgene. The promotor may be an inducible promotor which is inducible by e.g. a chemical inducer.

In one embodiment, the present invention provides a phage comprising the polynucleotide as described herein or the polynucleotide as described herein. The phage, also known as bacteriophage, may be any phage, such as for example a M13 phage, lambda phage, T4 phage or T7 phage. The phage may comprise the polynucleotide as described herein and be capable of providing expression of the peptide encoded by said polynucleotide. The phage may be able to present said peptide to the exterior environment such as for example in a phage display system.

In one embodiment, the present invention provides a host cell expressing the polypeptide as described herein, or comprising the polynucleotide or the vector as described herein. The host cell may be any host cell, such as for example a cell that harbours foreign molecules, viruses, or microorganisms or a cell that is capable of or has been introduced with DNA (or RNA), such as a bacterial cell acting as a host cell for DNA.

Composition and Method of Treatment

In one embodiment, a composition comprising one or more polypeptide(s) as described herein is provided. Said composition may be a pharmaceutical composition.

In a particular embodiment, the composition comprises a polypeptide derived from SEQ ID NO: 5 as described herein above.

In one embodiment, the composition comprises two polypeptides as described herein. In some embodiments, the composition comprises two polypeptides corresponding to SEQ ID NO: 1 and SEQ ID NO: 2, SEQ ID NO: 1 and SEQ ID NO: 3; SEQ ID NO: 1 and SEQ ID NO: 4; SEQ ID NO: 1 and SEQ ID NO: 5; SEQ ID NO: 1 and SEQ ID NO: 6; SEQ ID NO: 2 and SEQ ID NO: 3; SEQ ID NO: 2 and SEQ ID NO: 4; SEQ ID NO: 2 and SEQ ID NO: 5; SEQ ID NO: 2 and SEQ ID NO: 6; SEQ ID NO: 3 and SEQ ID NO: 4, SEQ ID NO: 3 and SEQ ID NO: 5; SEQ ID NO: 4 and SEQ ID NO: 5; SEQ ID NO: 4 and SEQ ID NO: 6 or SEQ ID NO: 5 and SEQ ID NO: 6.

In one embodiment, the composition comprises three polypeptides as described herein. In some embodiments, the composition comprises three polypeptides corresponding to SEQ ID NO: 1, SEQ ID NO: 2 and SEQ ID NO: 3; SEQ ID NO: 1, SEQ ID NO: 2 and SEQ ID NO: 4; SEQ ID NO: 1, SEQ ID NO: 2 and SEQ ID NO: 5; SEQ ID NO: 1, SEQ ID NO: 2 and SEQ ID NO: 6; SEQ ID NO: 1, SEQ ID NO: 3 and SEQ ID NO: 4; SEQ ID NO: 1, SEQ ID NO: 3 and SEQ ID NO: 5; SEQ ID NO: 1, SEQ ID NO: 3 and SEQ ID NO: 6; SEQ ID NO: 1, SEQ ID NO: 4 and SEQ ID NO: 5; SEQ ID NO: 1, SEQ ID NO: 4 and SEQ ID NO: 6; SEQ ID NO: 1, SEQ ID NO: 5 and SEQ ID NO: 6; SEQ ID NO: 2, SEQ ID NO: 3 and SEQ ID NO: 4; SEQ ID NO: 2, SEQ ID NO: 3 and SEQ ID NO: 5; SEQ ID NO: 2, SEQ ID NO: 3 and SEQ ID NO: 6; SEQ ID NO: 2, SEQ ID NO: 4 and SEQ ID NO: 5; SEQ ID NO: 2, SEQ ID NO: 4 and SEQ ID NO: 6; SEQ ID NO: 2, SEQ ID NO: 5 and SEQ ID NO: 6; SEQ ID NO: 3, SEQ ID NO: 4 and SEQ ID NO: 5; SEQ ID NO: 3, SEQ ID NO: 4 and SEQ ID NO: 6; SEQ ID NO: 3, SEQ ID NO: 5 and SEQ ID NO: 6 or SEQ ID NO: 4, SEQ ID NO: 5 and SEQ ID NO: 6.

In one embodiment, the composition comprises four polypeptides as described herein. In some embodiments, the composition comprises four polypeptides corresponding to SEQ ID NO: 1, SEQ ID NO: 2, SEQ ID NO: 3 and SEQ ID NO: 4; SEQ ID NO: 1, SEQ ID NO: 2, SEQ ID NO: 3 and SEQ ID NO: 5; SEQ ID NO: 1, SEQ ID NO: 2, SEQ ID NO: 3 and SEQ ID NO: 6; SEQ ID NO: 1, SEQ ID NO: 2, SEQ ID NO: 4 and SEQ ID NO: 5; SEQ ID NO: 1, SEQ ID NO: 2, SEQ ID NO: 4 and SEQ ID NO: 6; SEQ ID NO: 1, SEQ ID NO: 2, SEQ ID NO: 5 and SEQ ID NO: 6; SEQ ID NO: 1, SEQ ID NO: 3, SEQ ID NO: 4 and SEQ ID NO: 5; SEQ ID NO: 1, SEQ ID NO: 3, SEQ ID NO: 4 and SEQ ID NO: 6; SEQ ID NO: 1, SEQ ID NO: 3, SEQ ID NO: 5 and SEQ ID NO: 6; SEQ ID NO: 1, SEQ ID NO: 4, SEQ ID NO: 5 and SEQ ID NO: 6; SEQ ID NO: 2, SEQ ID NO: 3, SEQ ID NO: 4 and SEQ ID NO: 5; SEQ ID NO: 2, SEQ ID NO: 3, SEQ ID NO: 4 and SEQ ID NO: 6; SEQ ID NO: 2, SEQ ID NO: 3, SEQ ID NO: 5 and SEQ ID NO: 6; SEQ ID NO: 2, SEQ ID NO: 4, SEQ ID NO: 5 and SEQ ID NO: 6 or SEQ ID NO: 3, SEQ ID NO: 4, SEQ ID NO: 5 and SEQ ID NO: 6;

In one embodiment, the composition comprises five polypeptides as described herein. In some embodiments, the composition comprises five polypeptides corresponding to SEQ ID NO: 1, SEQ ID NO: 2, SEQ ID NO: 3, SEQ ID NO: 4 and SEQ ID NO: 5; SEQ ID NO: 1, SEQ ID NO: 2, SEQ ID NO: 3, SEQ ID NO: 4 and SEQ ID NO: 6; SEQ ID NO: 1, SEQ ID NO: 2, SEQ ID NO: 3, SEQ ID NO: 5 and SEQ ID NO: 6; SEQ ID NO: 1, SEQ ID NO: 2, SEQ ID NO: 4, SEQ ID NO: 5 and SEQ ID NO: 6; SEQ ID NO: 1, SEQ ID NO: 3, SEQ ID NO: 4, SEQ ID NO: 5 and SEQ ID NO: 6 or SEQ ID NO: 2, SEQ ID NO: 3, SEQ ID NO: 4, SEQ ID NO: 5 and SEQ ID NO: 6.

In one embodiment, the composition comprises six polypeptides as described herein. In one embodiment, the composition comprises six polypeptides corresponding to SEQ ID NO: 1, SEQ ID NO: 2, SEQ ID NO: 3, SEQ ID NO: 4, SEQ ID NO: 5 and SEQ ID NO: 6.

In one embodiment, the composition is formulated as a tablet, pill, capsule, lyophilizate, liquid preparation, liposome suspension, granules, patch, film, cream, ointment, gel, or nasal spray or inhalant.

In a separate embodiment, the composition is formulated as a liquid preparation, patch, film, cream, gel or ointment. Preferably, the composition is formulated as a liquid preparation.

The liquid preparation may be formulated in an ampoule, a pen or an autoinjector.

In one embodiment, the invention provides a polypeptide, a polynucleotide, a vector, a phage, a host cell or a composition as described herein for use as a medicament.

In one embodiment, the invention provides a polypeptide, a polynucleotide, a vector, a phage, a host cell or a composition as described herein for use in the treatment of envenomation.

In one embodiment, the invention provides use of a polypeptide, a polynucleotide, a vector, a phage, a host cell or a composition as described herein for the manufacture of a medicament for treatment of envenomation.

In one embodiment, the invention provides a method of treatment of envenomation, the method comprising administering to a subject in need thereof a therapeutically effective amount of a polypeptide, a polynucleotide, a vector, a phage, a host cell or a composition as described herein. The subject in need thereof may be a human or an animal, such as for example a cat, dog, cattle, horse, llama, alpaca or sheep. Said human may be neonatal or an infant.

In one embodiment, the polypeptide, the polynucleotide, the vector, the phage, the host cell or the composition as described herein is administered in combination with another antivenom or antitoxin, such as for example an antitoxin capable of neutralizing a neurotoxin, a cytotoxin or a hemotoxin. Such combination therapy may result in improved antivenom therapy. The terms "antivenom" and "antitoxin" are used interchangeably herein and refer to a compound which is capable of neutralizing, preventing or inhibiting the toxic activity of a venom or toxin.

The term 'neurotoxin' as used herein, refers to a biological, chemical, or physical agent capable of producing an adverse effect on the structure or function of the central and/or peripheral nervous system.

The term 'hemotoxin' as used herein, refers to a biological, chemical, or physical agent capable of destroying red blood cells, disrupt integrity of blood vessels, disrupt blood clotting, and/or cause organ degeneration and generalized tissue damage secondary to alterations associated with bleeding.

The term 'cytotoxin' as used herein, refers to a biological, chemical, or physical agent capable of being toxic to cells.

In one embodiment, the polypeptide, the polynucleotide, the vector, the phage, the host cell or the composition as described herein is administered via a route selected from the group consisting of intravenous, subcutaneous, intramuscular, intradermal, pulmonary, transdermal, topical and per oral.

In another embodiment, the route of administration is selected from the group consisting of subcutaneous, intramuscular, intradermal, transdermal and topical.

Preferably, the route of administration is intramuscular.

In one embodiment, the envenomation to be treated is caused by a snakebite, a lizard bite, a spider bite, an insect sting, a jellyfish sting, a scorpion sting or a cone snail sting.

In a preferred embodiment, the envenomation to be treated is caused by a snakebite, a spider bite, a scorpion sting or a bee sting. More preferably, the envenomation to be treated is caused by a snake bite.

In one embodiment, the envenomation is caused by a snakebite. The envenomation may be caused by a snakebite from for example a viperidae, for example from a *Bothrops* species, a *Agkistrodon* species, a *Protobothrops* species, a *Lachesis* species such as *Lachesis muta muta*, a *Bitis* species such as *Bitis caudalis*, an *Atropoides* species such as *Atropoides nummifer mexicanus* or a *Trimeresurus* species; from a sea snake, for example from an *Aipsurus laevis*; or from a land elapid, for example from a *Micrurus* species such as *Micrurus nigrocinctus* or from a *Dendroaspis* species such as *Dendroaspis polyepis*. Preferably, the envenomation is caused by a *Bothrops* species, more preferably from *Bothrops asper*. In preferred embodiments, the envenomation is caused by a snake selected from the group consisting of *Bitis caudalis, Atropoides nummifer mexicanus, Apisurus laevis, Lachesis muta muta, Micrurus nigrocintus, Dendroaspis polyepis* or *Bothrops asper*, most preferably the venom is from *Bitis caudalis, Atropoides nummifer mexicanus, Lachesis muta muta, Dendroaspis polyepis* or *Bothrops asper*.

Sequences

VNRMLELKIMDYGGG  SEQ ID NO: 1

QSVTMGPGLITHSPIHTQSK  SEQ ID NO: 2

DYDRIPDIPMLGGGG  SEQ ID NO: 3

SWEPYANPTRYKFHDW  SEQ ID NO: 4

DHWVWGWNYQYQPQEWHTES  SEQ ID NO: 5

NGYWSSQQYMQQAPMPWRIP  SEQ ID NO: 6

Items
1. An isolated non-natural polypeptide having myotoxin-neutralizing properties.
2. The polypeptide according to item 1, wherein the myotoxin is a phospholipase A$_2$.
3. The polypeptide according to any one of the preceding items, wherein the myotoxin is myotoxin II.
4. The polypeptide according to any one of the preceding items, wherein the myotoxin is from a snake venom.
5. The polypeptide according to any one of the preceding items, wherein the myotoxin is from a viperidae, a sea snake or a land elapid.
6. The polypeptide according to any one of the preceding items, wherein the myotoxin is from a *Bothrops* species, preferably from *Bothrops asper*, an *Agkistrodon* species, a *Protobothrops* species, a *Lachesis* species such as *Lachesis muta muta*, a *Bitis* species such as *Bitis caudalis*, an *Atropoides* species such as *Atropoides nummifer mexicanus*, a *Trimeresurus* species, an *Aipsurus* species such as an *Aipsurus laevis*, a *Micrurus* species such as *Micrurus nigrocinctus* or a *Dendroaspis* species such as *Dendroaspis polyepis*.
7. The polypeptide according to any one of the preceding items, said polypeptide comprising or consisting of an amino acid sequence selected from the group consisting of
   a) the amino acid sequence according to SEQ ID NO: 1, SEQ ID NO: 2, SEQ ID NO: 3, SEQ ID NO: 4, SEQ ID NO: 5, or SEQ ID NO: 6;
   b) a variant of SEQ ID NO: 1, SEQ ID NO: 2, SEQ ID NO: 3, SEQ ID NO: 4, SEQ ID NO: 5, or SEQ ID NO: 6, wherein said variant has at least 80% sequence identity to SEQ ID NO: 1, SEQ ID NO: 2, SEQ ID NO: 3, SEQ ID NO: 4, SEQ ID NO: 5, or SEQ ID NO: 6;
   c) a variant of SEQ ID NO: 1, SEQ ID NO: 2, SEQ ID NO: 3, SEQ ID NO: 4, SEQ ID NO: 5, or SEQ ID NO: 6, wherein said variant has between 1 and 10 amino acid substitutions and/or deletions as compared to SEQ ID NO: 1, SEQ ID NO: 2, SEQ ID NO: 3, SEQ ID NO: 4, SEQ ID NO: 5, or SEQ ID NO: 6;
   d) a fragment of SEQ ID NO: 1, SEQ ID NO: 2, SEQ ID NO: 3, SEQ ID NO: 4, SEQ ID NO: 5, or SEQ ID NO: 6, or a variant thereof having between 1 and 10 amino acid substitutions and/or deletions as compared to SEQ ID NO: 1, SEQ ID NO: 2, SEQ ID NO: 3, SEQ ID NO: 4, SEQ ID NO: 5, or SEQ ID NO: 6, such as between 1 and 5, for example between 1 and 3 amino acid substitutions and/or deletions as compared to SEQ ID NO: 1, SEQ ID NO: 2, SEQ ID NO: 3, SEQ ID NO: 4, SEQ ID NO: 5, or SEQ ID NO: 6;
   e) a fragment of SEQ ID NO: 1, SEQ ID NO: 2, SEQ ID NO: 3, SEQ ID NO: 4, SEQ ID NO: 5, or SEQ ID NO: 6, or a variant thereof having between 3 and 18 consecutive amino acids as compared to SEQ ID NO: 1, SEQ ID NO: 2, SEQ ID NO: 3, SEQ ID NO: 4, SEQ ID NO: 5, or SEQ ID NO: 6, such as between 5 and 15, for example between 7 and 12 consecutive amino acids as compared to SEQ ID NO: 1, SEQ ID NO: 2, SEQ ID NO: 3, SEQ ID NO: 4, SEQ ID NO: 5, or SEQ ID NO: 6;
   f) an amino acid sequence differing from SEQ ID NO: 1, SEQ ID NO: 2, SEQ ID NO: 3, SEQ ID NO: 4, SEQ ID NO: 5, or SEQ ID NO: 6 by truncation at the N-terminus by at least one amino acid, such as between 1 and 10 amino acids, for example between 1 and 5 amino acids, or a variant thereof having between 1 and 10 amino acid substitutions and/or deletions as compared to SEQ ID NO: 1, SEQ ID NO: 2, SEQ ID NO: 3, SEQ ID NO: 4, SEQ ID NO: 5, or SEQ ID NO: 6; and
   g) an amino acid sequence differing from SEQ ID NO: 1, SEQ ID NO: 2, SEQ ID NO: 3, SEQ ID NO: 4, SEQ ID NO: 5, or SEQ ID NO: 6 by truncation at the C-terminus by at least one amino acid, such as between 1 and 10 amino acids, for example between 1 and 5 amino acids, or a variant thereof having between 1 and 10 amino acid substitutions and/or deletions as compared to SEQ ID NO: 1, SEQ ID NO: 2, SEQ ID NO: 3, SEQ ID NO: 4, SEQ ID NO: 5, or SEQ ID NO: 6.
8. The polypeptide according to any one of the preceding items, wherein said variant has at least 90% sequence identity to SEQ ID NO: 1, SEQ ID NO: 2, SEQ ID NO: 3, SEQ ID NO: 4, SEQ ID NO: 5, or SEQ ID NO: 6, such as at least 95%, for example at least 97% sequence identity to SEQ ID NO: 1, SEQ ID NO: 2, SEQ ID NO: 3, SEQ ID NO: 4, SEQ ID NO: 5, or SEQ ID NO: 6.
9. The polypeptide according to any one of the preceding items, wherein said polypeptide has a length of less than 100, 95, 90, 85, 80, 75, 70, 65, 60, 55, 50, 45, 40, 35, 30, 25, 20, 19, 18, 17, 16, 15, 10 or 5 amino acids.
10. The polypeptide according to any one of the preceding items, wherein the amino acid substitutions are conservative substitutions.

11. The polypeptide according to any one of the preceding items, wherein the polypeptide comprises one or more non-natural amino acid(s).
12. The polypeptide according to any one of the preceding items, wherein the polypeptide comprises one or more D-amino acid(s).
13. The polypeptide according to any one of the preceding items, wherein the polypeptide is a peptoid.
14. The polypeptide according to any one of the preceding items, wherein the polypeptide is alkylated at one or more backbone amide nitrogen(s).
15. The polypeptide according to any one of the preceding items, wherein the polypeptide is acetylated at the N-terminus.
16. The polypeptide according to any one of the preceding items, wherein the polypeptide comprises a C-terminal amide.
17. The polypeptide according to any one of the preceding items, wherein the polypeptide has been cyclized.
18. The polypeptide according to any one of the preceding items, wherein the polypeptide is modified by a post translational modification, such as for example modified by phosphorylation, methylation or acylation.
19. The polypeptide according to any one of the preceding items, wherein said polypeptide further comprises one or more moieties conjugated to said polypeptide.
20. The polypeptide according to item 19, wherein the one or more moieties are selected from the group consisting of albumin, albumin binding moiety, fatty acids, polyethylene glycol (PEG), biotin, acylation groups, proteins, peptides, nanobodies, antibodies and antibody fragments.
21. The polypeptide according to any of items 19 to 20, wherein said polypeptide and the one or more moieties are conjugated to each other by a linker.
22. The polypeptide according to any one of items 1 to 21, wherein the polypeptide has been immobilized on a solid support.
23. A polynucleotide encoding the polypeptide according to any one of the preceding items.
24. The polynucleotide according to item 23, wherein the polynucleotide is codon optimized.
25. A vector comprising the polynucleotide according to any one of items 23 to 24.
26. A phage comprising the polypeptide according to any one of items 1 to 22 or the polynucleotide according to any one of items 23 to 24.
27. A host cell expressing the polypeptide according to any one of items 1 to 22, or comprising the polynucleotide according to any one of items 23 to 24, the vector according to item 25 or the phage according to item 26.
28. The polypeptide according to any one of items 1 to 22 further having α-cobratoxin-neutralizing properties.
29. A composition comprising a polypeptide according to any one of items 1 to 22.
30. The composition according to item 28, wherein the composition is a pharmaceutical composition.
31. The composition according to any one of items 28 to 30, wherein the composition is formulated as a tablet, pill, capsule, lyophilizate, liquid preparation, liposome suspension, granules, patch, film, cream, ointment, gel, nasal spray or inhalant.
32. The composition according to any one of items 28 to 30, wherein the composition is formulated as a liquid preparation, patch, film, cream, gel or ointment.
33. The composition according to any one of items 28 to 30, wherein the composition is formulated as a liquid preparation.
34. A method of neutralizing a venom, the method comprising contacting a polypeptide according to any one of items 1 to 22, the polynucleotide according to any one of items 23 to 24, the vector according to item 25, the phage according to item 26, the host cell according to item 27 or the composition according to any one of items 28 to 33 to said venom.
35. The method according to item 34, wherein the venom comprises a myotoxin.
36. The method according to item 34, wherein the venom comprises a phospholipase $A_2$.
37. The method according to item 34, wherein the venom comprises myotoxin II.
38. The method according to item 34, wherein the venom is from a snake.
39. The method according to item 34, wherein the venom is from a viperidae, a sea snake or a land elapid.
40. The method according to item 34, wherein the venom is from a *Bothrops* species, preferably from *Bothrops asper*.
41. A method of improving antivenom therapy by co-administering to a subject in need thereof the polypeptide according to any one of items 1 to 22, the polynucleotide according to any one of items 23 to 24, the vector according to item 25, the phage according to item 26, the host cell according to item 27 or the composition according to any one of items 28 to 33 with one or more additional antivenoms.
42. The polypeptide according to any one of items 1 to 22, the polynucleotide according to any one of items 23 to 24, the vector according to item 25, the phage according to item 26, the host cell according to item 27 or the composition according to any one of items 28 to 33 for use as a medicament.
43. The polypeptide according to any one of items 1 to 22, the polynucleotide according to any one of items 23 to 24, the vector according to item 25, the phage according to item 26, the host cell according to item 27 or the composition according to any one of items 28 to 33 for use in the treatment of envenomation.
44. The polypeptide according to any one of items 1 to 22, the polynucleotide according to any one of items 23 to 24, the vector according to item 25, the phage according to item 26, the host cell according to item 27 or the composition according to any one of items 28 to 33 for use in the manufacture of a medicament.
45. The polypeptide according to any one of items 1 to 22, the polynucleotide according to any one of items 23 to 24, the vector according to item 25, the phage according to item 26, the host cell according to item 27 or the composition according to any one of items 28 to 33 for use in a method of treatment of envenomation.
46. Use of the polypeptide according to any one of items 1 to 22, the polynucleotide according to any one of items 23 to 24, the vector according to item 25, the phage according to item 26, the host cell according to item 27 or the composition according to any one of items 28 to 33 for the manufacture of a medicament.
47. Use of the polypeptide according to any one of items 1 to 22, the polynucleotide according to any one of items 23 to 24, the vector according to item 25, the phage according to item 26, the host cell according to item 27 or the composition according to any one of items 28 to 33 for the manufacture of a medicament for treatment of envenomation.
48. A method of treatment of envenomation, the method comprising administering to a subject in need thereof a therapeutically effective amount of a polypeptide according to any one of items 1 to 22, the polynucleotide according to any one of items 23 to 24, the vector according to item 25, the phage according to item 26, the host cell according to item 27 or the composition according to any one of items 28 to 33.

49. The method according to item 48, wherein the polypeptide according to any one of items 1 to 22, the polynucleotide according to any one of items 23 to 24, the vector according to item 25, the phage according to item 26, the host cell according to item 27 or the composition according to any one of items 28 to 33 is administered in combination with one or more additional antitoxin(s), such as for example an antitoxin capable of neutralizing a neurotoxin, a cytotoxin or a hemotoxin.

50. The method according to any one of items 48 to 49, wherein the route of administration is selected from the group consisting of intravenous, subcutaneous, intramuscular, intradermal, pulmonary, transdermal, topical and per oral.

51. The method according to any one of items 48 to 49, wherein the route of administration is selected from the group consisting of subcutaneous, intramuscular, intradermal, transdermal and topical.

52. The method according to any one of items 48 to 49, wherein the route of administration is intramuscular.

53. The method according to any one of items 48 to 52, wherein said subject is selected from the group consisting of human, cat, dog, cattle, horses, llamas, alpacas, and sheep.

54. The polypeptide for the use according to item 43 or the method according to any one of items 48 to 53, wherein said envenomation is caused by a snakebite, a lizard bite, a spider bite, an insect sting, a jellyfish sting, a scorpion sting or a cone snail sting.

55. The polypeptide for the use according to item 43 or the method according to any one of items 48 to 53, wherein said envenomation is caused by a snakebite, a spider bite, a scorpion sting or a bee sting.

56. The polypeptide for the use according to item 43 or the method according to any one of items 48 to 53, wherein said envenomation is caused by a snakebite.

57. The polypeptide for the use according to item 43 or the method according to any one of items 48 to 53, wherein said envenomation is caused by a snakebite from a viperidae, a sea snake or a land elapid.

58. The polypeptide for the use according to item 43 or the method according to any one of items 48 to 53, wherein said envenomation is caused by a snakebite, preferably from a *Bothrops* species, preferably from *Bothrops asper*, an *Agkistrodon* species, a *Protobothrops* species, a *Lachesis* species such as *Lachesis muta muta*, a *Bitis* species such as *Bitis caudalis*, an *Atropoides* species such as *Atropoides nummifer mexicanus*, a *Trimeresurus* species, an *Aipsurus* species such as an *Aipsurus laevis*, a *Micrurus* species such as *Micrurus nigrocinctus* or a *Dendroaspis* species such as *Dendroaspis polyepis*.

EXAMPLES

Example 1: Materials and Methods

Myotoxin II was purified to homogeneity from venom of *Bothrops asper* by chromatographic separation. Aliquots of 1.1 µg myotoxin II in 10 µL PBS were made and stored at −80° C. until further use. The phage libraries used is a TriCo-16™ Phage Display 16-mer Random Peptide Library and a Trico-20™ Phage display 20-mer Random Peptide Library.

Coating

Wells were coated using a Nunc Maxisorp® Immunoplate. 1.1 µg myotoxin II (MT-II) in 10 µL PBS were dissolved in 100 µL PBS. As control, one well was left uncoated. The Maxisorp plate was then stored overnight at 4° C.

Panning and Amplification of Phages

A colony from a *E. coli* TG1 culture was dissolved in a vial containing 9 mL 2×YT (2× yeast extract tryptone) medium and placed in incubator at 37° C. to be used later. The coated wells were blocked with 100 µL PBS+4% skimmed milk and placed on a mixer for 1 hour at room temperature. To remove any unbound toxin, the wells were washed with 3×100 µL PBS. The phage library was prepared by mixing 110 µL PBS with 5 µL from a 16-mer random peptide library and 5 µL from a 20-mer random peptide library. The phage library was then mixed with 120 µL PBS+4% skimmed milk. From this solution, 100 µL was added to each well. The wells were incubated for 1 hour at room temperature while shaking. In order to remove unbound phages, the wells were washed with 10×100 µL PBS. To separate the phages bound to the toxin and elute the phages, 100 µL of 10 mM Glycine-HCl, pH 2.5, was added to each well, and the Maxisorp plate was placed on incubator for 10 minutes in room temperature while shaking. To neutralize acidity, the solutions on the plates were transferred to Eppendorf tubes containing 1 µL of 2M Tris-Base and vortexed.

500 µL of the exponentially growing *E. coli* TG1 culture was added to each eppendorf tube and incubated for 20 minutes at 37° C. This solution was then transferred to beakers containing 10 mL 2×YT and incubated overnight at 37° C.

Harvest of Phage Libraries

To remove TG1 cells, the culture from previous day were transferred to a centrifuge tube and centrifuged at 10000 rpm for 10 minutes (Sorvall Evolution™ RC Superspeed Centrifuge). The supernatant was transferred to another centrifuge tube containing 1 mL precipitation buffer (20% PEG6000, 2.5M NaCl), and kept on ice for 1 hour. To precipitate the phages, the tubes were centrifuged again at 13000 rpm for 15 minutes. The supernatant was discarded, except for 1 ml that was left to resuspend the pellet containing the phages. The 1 mL solution was transferred to a new Eppendorf tube, and centrifuged again at 13000×g for 5 minutes (Ole Dick Microcentrifuge). Supernatant was again discarded and the Eppendorf tube centrifuged again at 13000×g for 20 seconds to discard remaining supernatant. To release the phages, the pellet was suspended in 500 µL PBS. To precipitate the remaining cell debris, the Eppendorf tube was centrifuged one last time at 13000×g for 5 minutes. The phage library was then added to a new Eppendorf tube and stored at −20° C. until further needed.

Phages derived from the control wells coated with PBS were referred to as "Control library" and phages derived from wells coated with myotoxin II referred to as "MT-II library".

Titer Test

Petri plates with incorporated IPTG and Xgal were incubated at 37° C. 1 hour prior to use. Dilution series were made from both the control library and MT-II library. Dilutions series were made by taking 10 µL of the libraries and dilute them in 990 µL PBS, making concentrations of $10^{-2}$, $10^{-4}$, $10^{-6}$, $10^{-8}$, $10^{-10}$. From each dilution, 100 µL was transferred to a new Eppendorf tube, and mixed with 100 μL of exponentially growing TG1 culture. This solution was then added to the Wasserman tube containing liquid top agar (3.5 mL) at 45° C., and quickly spread out on IPTG/XGAL agar plates. The plates were incubated overnight at 37° C.

The plates were analyzed manually by counting the plaques. The phage titer was calculated by using the following formula:

Titer=(plaque forming units(pfu))/(input volume of phages*dilution factor)

Enzyme-Linked Immunosorbent Assay (ELISA)

An ELISA was performed in order to confirm binding of the phages to myotoxin II. For each of the 5 panning rounds with the MT-II libraries to be tested, two wells were coated as described above, one with MT-II and one control well with PBS. The wells were blocked with 100 μL 2% BSA in PBS and incubated for 1 hour at room temperature while shaking. To remove unbound toxin, wells were washed with 5×100 μL 0.05% Tween in PBS.

Various amount of phage volume ranging from 5 μL to 50 μL was mixed with 2% BSA in PBS and added to all wells, and incubated for 2 hours at room temperature while shaking. Wells were washed with 5×100 μL 0.05% Tween in PBS to remove unbound phages. A solution of 3 μL anti-M13-HRP antibody and 3 mL 2% BSA in PBS was prepared and 100 μL from this was added to all wells, and incubated for 2 hours at room temperature while shaking. Wells were washed with 5×100 μL 0.05% Tween in PBS in order to remove unbound antibodies.

One tablet of 2 mg o-phenylenediamine (ODP) was dissolved in 2.5 mL of sterile $H_2O$ and 2.5 μL $H_2O_2$. 100 μL of this solution was added to all wells. Neither the tube containing the solution nor the plate was exposed to light except when checking for color formation. The reaction was stopped by adding 100 μL of 1M $H_2SO_4$ after sufficient color formation was appreciated. The absorbance was measured at 490 nm (VersaMax Tunable Microplate reader, Molecular Devices).

Isolation of Monoclonal Phages

The phage libraries with significant absorbance measurement were selected. A new titer test was done for these, and single plaques were picked out with a Pasteur pipette and transferred to Eppendorf tubes containing 1 ml of LB media and left at 37° C. overnight. An ELISA was performed to confirm binding. Then 100 μL of specific clone was mixed with 500 μL of exponentially growing TG1 *E. coli* and amplified as described above. The monoclonal phages were then harvested as described above. A new ELISA assay was performed using the procedure described above. The phages that showed a significant absorbance was used for an additional ELISA, together with monoclonal phages from a previous study using the same toxin and the same phage library.

Isolation of DNA from Monoclonal Phages

The selected monoclonal phages from the ELISA were characterized further by isolating their DNA, in order to obtain the DNA sequences. The selected clones were amplified and harvested as described above. The phages were resuspended in 300 μL PBS instead of 500 μL. To each Eppendorf tube containing the phage, 300 μL of phenol in chloroform was added, and the tubes were centrifuged at 8000×g for 5 minutes (Ole Dick Microcentrifuge). The upper phase containing the phages was transferred to a new Eppendorf tube. To the phage solution, 30 μL of 3 M sodium acetate was added, and then 600 μL of 96% ethanol. The tubes were then placed in −80° C. freezer for 10 minutes, followed by 10 minutes in −20° C. freezer. The precipitated DNA was then centrifuged at 4° C., 20000×g for 20 minutes. The supernatant was carefully removed and the pellet was resuspended in 250 μL 70% ethanol, and whirl-mixed for 10 seconds. Eppendorf tubes were then centrifuged again at 20000×g for 5 minutes, and the supernatant was discarded. To remove remaining ethanol and water, the pellet was dried for 20 minutes in a vacuum centrifuge (Speedvac Concentrator, Savant). The pellet was resuspended in 20 μL of sterile $H_2O$.

Gel Electrophoresis

The matrix was a 1% agarose gel (2 g of agarose in 200 mL 1×Tris Acetate-EDTA buffer) with 4 drops of ethidium bromide. From each sample 5 μL was mixed with 1 μL DNA loading dye and added to each well. As reference, one well contained 1 kb DNA ladder. Voltage was set to 115 volts, each experiment ran for 45 minutes, and the gel was then analyzed using UV detection. The samples that showed positive results were sent to sequencing at Eurofins Genomics (Eurofins MWG Operon).

Dilution Series

In order to obtain the most optimal dilution for the phages, dilution series of selected clones were made. Wells were coated with MT-II or left uncoated as described above. Phages were diluted in PBS: 1/10, 1/20, 1/50, 1/100, 1/500 and 1/1000, and tested in triplicates. An ELISA was performed for these dilutions.

Cross Reactivity

To see if the phages bind to more than one toxin, a cross reactivity study was performed. The toxin used were myotoxin I (MT-I) from *Bothrops asper, a*-cobra toxin (a-cbtx) from *Naja kaouthia*. In order to investigate if the phages bind to protein in the blood, human serum albumin was also used. Aliquots of 1.1 μg in 10 μL PBS of each toxin, including HSA were used for the coating. PBS was used as a negative control, and myotoxin II as positive control. The toxins were tested in triplicates and the ELISA assay was performed as described above. For the human serum albumin, the blocking agent 2% BSA in PBS was replaced by 4% skimmed milk.

Example 2: Identification of Binders

Phage display screening using a 16- and 20-mer library was performed in order to identify phages displaying binding affinity towards myotoxin II. The phage display experiment included a total of five panning rounds (FIG. 1).

Prior to each panning rounds, the concentration of the phage libraries was determined using a titer test (table 1). For the first two panning rounds, no obvious difference between the toxin library and the control library was observed. For the titer test prior to the 3$^{rd}$ panning round, the plate was overloaded with clones and the concentration could not be determined. The titer test prior to the 4$^{th}$ and the 5$^{th}$ panning rounds showed no clones in the control wells, indicating that the corresponding phage libraries could contain specific binders to myotoxin II.

TABLE 1

| | Titer tests result from the 5 panning rounds. | | | | | |
|---|---|---|---|---|---|---|
| | 1st panning | | 2nd panning | | 3rd panning | |
| Library | MT II | Control | MT II | Control | MT II | Control |
| Titer (pfu/ml) | $1.2 \times 10^{12}$ | $7.1 \times 10^{11}$ | $3.1 \times 10^{12}$ | $3.0 \times 10^{12}$ | n/a | n/a |
| Ratio (MTII/control) | 1.6/1 | | 1/1 | | | |

| | 4th panning | | 5th panning | |
|---|---|---|---|---|
| Library | MT II | Control | MT II | Control |
| Titer (pfu/ml) | $4.3 \times 10^{12}$ | 0 | $1 \times 10^{11}$ | 0 |
| Ratio (MTII/control) | 1/0 | | 1/0 | |

For each of the 5 panning rounds, a polyclonal ELISA was performed to identify binding of the phages to myotoxin II. In most of the panning rounds, the signal from the control wells was high, indicating the presence of unspecific binders (FIG. 2). However, the fourth panning round showed a low signal from the control wells, and this library was therefore chosen for identification of specific binders. This library was amplified and monoclonal phages were isolated and tested in a second ELISA analysis (FIG. 3).

To ensure that the identified phages were specific binders to myotoxin II, only clones which showed a low signal in the control well were selected for further analysis. The selected clones were analysed in an additional ELISA analysis to confirm binding (FIG. 4). Based on the ELISA, clone nr 1.1 (SEQ ID NO: 1), 1.2 (SEQ ID NO: 2), 1.4 (SEQ ID NO: 3), 1.8 (SEQ ID NO: 4), 1.9 (SEQ ID NO: 5) and 4.10 (SEQ ID NO: 6) showed the greatest difference between toxin coated wells and control, indicating the presence of specific binders to myotoxin II.

In conclusion, this example demonstrates that peptides which are specific binders to myotoxin II can be accumulated from the phage display library through multiple panning rounds.

Example 3: Isolation of DNA from Hits, Sequence Analysis and Analysis of Peptide Properties The DNA from the selected phages was isolated and separated using a standard DNA purification kit (QIAprep® Spin) and DNA purity verified using gel electrophoresis. The peptides were sequenced and the peptide sequences are shown in Table 2.

The properties of the peptides were predicted and are shown in table 2. The estimated half-lives of the peptides were predicted using ExPasy Protparam Tool (web.expasy.org/protparam/) and are estimated as in vitro half-lives in mammalian reticulocytes. Water solubility was predicted using PepCalc (pepcalc.com/) as an indicator for the solubility in body fluids having an impact on bioavailability in further drug development.

TABLE 2

Peptide sequences and properties

| Clone | SEQ ID NO: | Sequence | Length (aa) | Mass (Da) | Water solubility* | Half-life (h)** |
|---|---|---|---|---|---|---|
| 1.1 | 1 | VNRMLELKIMDYGGG | 15 | 1696.0 | Good | 100 |
| 1.2 | 2 | QSVTMGPGLITHSPIHTQSK | 20 | 2119.4 | Poor | 0.8 |
| 1.4 | 3 | DYDRIPDIPMLGGGG | 15 | 1575.7 | Good | 1.1 |
| 1.8 | 4 | SWEPYANPTRYKFHDW | 16 | 2097.3 | Good | 1.9 |
| 1.9 (JB0006) | 5 | DHWVWGWNYQYQPQEWHTES | 20 | 2676.7 | Poor | 1.1 |
| 4.10 | 6 | NGYWSSQQYMQQAPMPWRIP | 20 | 2468.7 | Poor | 1.4 |

*predicted using PepCalc,
**predicted using ExPasy Protparam Tool.

The clones which showed the highest affinity in the ELISAs (1.1 (SEQ ID NO: 1), 1.2 (SEQ ID NO: 2), 1.4 (SEQ ID NO: 3), 1.8 (SEQ ID NO: 4), 1.9 (SEQ ID NO: 5) and 4.10 (SEQ ID NO: 6)) vary in their predicted half-life, ranging from 0.8 to up to 100 hours. Of these, only three of them (1.1 (SEQ ID NO: 1), 1.4 (SEQ ID NO: 3) and 1.8 (SEQ ID NO: 4)) have an estimated good water solubility.

Example 4: Titration of Peptides

The clones 1.1 (SEQ ID NO: 1), 1.2 (SEQ ID NO: 2), 1.4 (SEQ ID NO: 3), 1.8 (SEQ ID NO: 4), 1.9 (SEQ ID NO: 5) and 4.10 (SEQ ID NO: 6) were re-amplified and tested at different dilutions in an ELISA to identify the clones having the highest specificity of binding, i.e. having the lowest control signal.

For all of the clones tested, a difference between the wells coated with toxin and the control wells (uncoated) was observed at the lowest dilutions (FIG. 5). Clone 1.1 (SEQ ID NO: 1), 1.2 (SEQ ID NO: 2), 1.4 (SEQ ID NO: 3) and 1.8 (SEQ ID NO: 4) showed a low difference for the dilutions of 1/100 and 1/1000, and also a lower signal from the toxin coated wells in the lower dilutions. Clones 1.9 (SEQ ID NO: 5) and 4.10 (SEQ ID NO: 6) showed the highest signals and also the highest signal to noise ratio in all of the dilutions, indicating the presence of specific binders.

Example 5: Cross Reactivity Studies

The clones were analyzed for their selectivity of binding different toxins. Based on the results of example 4, the two dilutions that showed the highest signal to noise ratio were selected for the cross reactivity study. These were 1/10 and 1/20 from clone 1.1 (SEQ ID NO: 1), 1.2 (SEQ ID NO: 2), 1.4 (SEQ ID NO: 3) and 1.8 (SEQ ID NO: 4), and 1/20 and 1/50 for clone 1.9 (SEQ ID NO: 5) and 4.10 (SEQ ID NO: 6).

Results from the cross reactivity ELISA (FIG. 6) showed that all of the tested clones were binding to myotoxin I, α-cobra toxin and myotoxin II. None of the clones were binding to human serum albumin control. Most of the clones showed similar signal intensity for binding to myotoxin I and II, clone 1.1 (SEQ ID NO: 1) to a lesser extent. Clones 1.9 (SEQ ID NO: 5) and 4.10 (SEQ ID NO: 6) showed the highest signal intensity and the best signal to noise ratio.

Example 6: In Vitro Myotoxin II Cell Toxicity in Presence of Peptide

The murine myogenic cell line C2C12 (ATCC code CRL-1772) was used to assess inhibition of cell toxicity. Confluent cells were differentiated for 5-6 days to obtain myotubes. A quantity of 10 μg of myotoxin II was diluted in assay medium (Dulbecco's modified Eagle Medium supplemented with 1% fetal bovine serum), preincubated at 37° C. for 30 min with or without 900 μM of peptide 1.9 (SEQ ID NO: 5) and added in a final volume of 100 μL. Wells that contained medium alone (0% cytotoxicity), or 0.1% Triton X-100 in medium (100% cytotoxicity) were used as controls. The activity of lactic dehydrogenase (LDH) released by damaged cells was quantified in 50 μL of supernatants using a kinetic assay (LDH-P Mono, Biocon Diagnostik, Voehl-Marienhagen, Germany) after 3 h at 37° C. Assays were performed in triplicate wells.

The presence of 900 μM of peptide 1.9 (SEQ ID NO: 5) abolished almost completely the cytotoxicity of Myotoxin II (4% toxicity against 87% toxicity).

This example demonstrates that a concentration of 900 μM of peptide 1.9 (SEQ ID NO: 5) almost completely neutralizes myotoxin II toxicity in cells.

Example 7: In Vivo Myotoxin II Toxicity in Presence of Peptide

A dose of 50 μg of Myotoxin II, previously incubated at 37° C. for 30 min in PBS with 0, 20, 100 or 900 μM of peptide 1.9 (SEQ ID NO: 5), was injected in the right gastrocnemius muscle of CD-1 mice (18-20 g, 5 mice each group) using a total volume of 50 μL. Controls were injected with 50 μL PBS incubated at the same conditions. The activity of plasma creatine kinase (CK; E.C. 2.7.3.2) was measured after 3 h using a kinetic assay (CK-Nac, Biocon Diagnostik, Voehl-Marienhagen, Germany) using 4 μL plasma aliquots obtained from centrifuged blood samples, collected from the tail into heparinized capillaries. Enzyme activity was expressed in U/L.

The presence of 900 μM of peptide 1.9 (SEQ ID NO: 5) neutralized the myotoxicity of Myotoxin II, when compared with controls.

This example demonstrates that a concentration of 900 μM peptide 1.9 (SEQ ID NO: 5) neutralized myotoxin II in a mouse model.

Example 8: Affinity Pull-Down Experiments

Agarose-streptavidin beads loaded with C-terminally biotinylated JB006 (SEQ ID NO: 5) were incubated with raw B. asper venom overnight at 4° C. The beads were washed extensively with PBS buffer and the bound protein content was eluted using glycine HCl buffer (100 mM, pH=2.8). All fractions were analyzed using by SDS-PAGE and stained with Coomassie blue. Results are shown in FIG. 9.

The strong band in the elution fractions contains Myotoxin-I/III and Myotoxin-II, which was confirmed by pull-down experiments using purified toxins. The elution fraction was further analyzed using MALDI-TOF MS and several masses correlating to other D49 or K49 PLA2 toxins were found. The majority of these PLA2s are not further characterized in the literature.

Example 9: Cross Affinity of JB006-Phage Clone in ELISA Experiments

ELISA experiments were performed using the JB006 (SEQ ID NO: 5) expressing phage clone to screen for cross affinity towards other relevant snake toxins. Results are shown in FIG. 10.

Venoms from the following snakes (signal/control >4) were identified as additional potential targets for cross inhibition of the JB006 peptide:

*Lachesis muta muta*
*Dendroaspis polyepis*
*Bitis caudalis*
*Atropoides nummifer mexicanus*

Example 10: Fluorescence Polarization for Studying Aggregation and Binding of JB006 and Analogues The binding of JB006 (SEQ ID NO: 5) to Myotoxin-II was confirmed using a fluorescence polarization (FP) binding assay (FIG. 11A). In the course of this study it was discovered that JB006 most likely is self-assembling or aggregating, which leads to an artificial increase of fluorescence polarization due to the decreased rotational freedom of the TAMRA-labeled JB006 probe (FIG. 11B). This effect eliminates the use of fluorescence polarization for aggregating peptides. All JB006 analogues were tested for their self-assembling or aggregating ability and only 3 peptides (W3A, W5A and Y11D-Y) were found in the alanine and D-amino acid scan, which did not artificially increase the FP signal of the TAMRA-probe. The truncation series revealed that all peptides <15 amino acids did not artificially increase the FP signal. However, none of selected peptides was able to outcompete the TAMRA-JB006 probe in a binding assay against Myotoxin-II (FIG. 11C).

Example 11: Structural Studies Using Circular Dichroism (CD) Spectroscopy

The secondary structure determination of JB006 (SEQ ID NO: 5) in solution using CD spectroscopy showed the characteristic double minima of a helical structure at ~208 nm and ~220 nm at pH 7.0 (FIG. 12A). The signature of the recorded CD spectra was very pH depending and even a shift to 7.4 changed the shape significantly. The peptide was unfolded and had no secondary structure at low or high pH (FIG. 12B) but remarkably even at pH 8 not folding was observed. The biotinylated JB006 analogue, which was used for affinity pull-down experiments, showed helical folding at 7.4, the pH used in in these experiments (FIG. 12C). The non-aggregating truncated analogues of JB006 (<15AA) showed no folding at neutral pH as well as the three non-aggregating single mutants (data not shown).

No unfolded JB006 analogue was able to outcompete the TAMRA-JB006 probe in the FP binding assay. It is likely that the TAMRA label does not interfere with the folding as seen for the biotin label (FIG. 12C), indicating that the folding may play a role in the binding to Myotoxin-II.

The non-aggregating truncated analogues of JB006 (<15AA) showed no folding at neutral pH (FIG. 4D) as well as the three non-aggregating single mutants (FIG. 4E). No unfolded JB006 analogue was able to outcompete the TAMRA-JB006 probe in the FP binding assay. It is likely that the TAMRA label does not interfere with the folding as seen for the biotin label (FIG. 4C), so it seems that the folding plays a role in the binding to Myotoxin-II.

The invention claimed is:

1. A polypeptide having myotoxin-neutralizing properties, said polypeptide comprising of:

a) the amino acid sequence as set forth in SEQ ID NO: 5 or b) a variant of SEQ ID NO: 5, wherein said variant has at least 90% sequence identity to SEQ ID NO: 5.

2. The polypeptide according to claim 1, wherein said variant has at least 95% sequence identity to SEQ ID NO: 5.

3. The polypeptide according to claim 1, wherein said variant has at least 96% sequence identity to SEQ ID NO: 5.

4. The polypeptide according to claim 1, wherein said variant has at least 97% sequence identity to SEQ ID NO: 5.

5. The polypeptide according to claim 1, wherein said variant has at least 98% sequence identity to SEQ ID NO: 5.

6. The polypeptide according to claim 1, wherein said variant has at least 99% sequence identity to SEQ ID NO: 5.

7. The polypeptide according to claim 1, wherein said variant has 100% sequence identity to SEQ ID NO: 5.

8. The polypeptide according to claim 1 further having α-cobratoxin-neutralizing properties.

9. The polypeptide according to claim 1, for use as a medicament.

10. The polypeptide according to claim 9, for use in the treatment of envenomation.

11. The polypeptide, for the use according to claim 10, wherein said envenomation is caused by a snakebite from a *Bothrops* species, an *Agkistrodon* species, a *Protobothrops* species, a *Lachesis* species, a *Bitis* species, an *Atropoides* species, a *Trimeresurus* species, an *Aipsurus* species, a *Micrurus* species, or a *Dendroaspis* species.

12. The polypeptide, for the use according to claim 11, wherein the *Bothrops* species is *Bothrops asper.*

13. The polypeptide, for the use according to claim 11, wherein the *Lachesis* species is *Lachesis muta muta.*

14. The polypeptide, for the use according to claim 11, wherein the *Bitis* species is *Bitis caudalis.*

15. The polypeptide, for the use according to claim 11, wherein the *Atropoides* species is *Atropoides nummifer mexicanus.*

16. The polypeptide, for the use according to claim 11, wherein the *Aipsurus* species is an *Aipsurus laevis.*

17. The polypeptide, for the use according to claim 11, wherein the *Micrurus* species is an *Micrurus nigrocinctus.*

18. The polypeptide, for the use according to claim 11, wherein the *Dendroaspis* species is an *Dendroaspis polyepis.*

19. A composition comprising a polypeptide according to claim 1, optionally comprising pharmaceutically acceptable excipients.

20. A method of neutralizing a venom from a snake, spider, scorpion, or bee, the method comprising contacting a polypeptide according to claim 1 to said venom.

* * * * *

SEQUENCE LISTING

```
<160> NUMBER OF SEQ ID NOS: 6

<210> SEQ ID NO 1
<211> LENGTH: 15
<212> TYPE: PRT
<213> ORGANISM: Artificial sequence
<220> FEATURE:
<223> OTHER INFORMATION: Peptide, clone 1.1

<400> SEQUENCE: 1

Val Asn Arg Met Leu Glu Leu Lys Ile Met Asp Tyr Gly Gly Gly
1               5                   10                  15

<210> SEQ ID NO 2
<211> LENGTH: 20
<212> TYPE: PRT
<213> ORGANISM: Artificial sequence
<220> FEATURE:
<223> OTHER INFORMATION: Peptide, clone 1.2

<400> SEQUENCE: 2

Gln Ser Val Thr Met Gly Pro Gly Leu Ile Thr His Ser Pro Ile His
1               5                   10                  15

Thr Gln Ser Lys
            20

<210> SEQ ID NO 3
<211> LENGTH: 15
<212> TYPE: PRT
<213> ORGANISM: Artificial sequence
<220> FEATURE:
<223> OTHER INFORMATION: Peptide, clone 1.4

<400> SEQUENCE: 3

Asp Tyr Asp Arg Ile Pro Asp Ile Pro Met Leu Gly Gly Gly Gly
1               5                   10                  15

<210> SEQ ID NO 4
<211> LENGTH: 16
<212> TYPE: PRT
<213> ORGANISM: Artificial sequence
<220> FEATURE:
<223> OTHER INFORMATION: Peptide, clone 1.8

<400> SEQUENCE: 4

Ser Trp Glu Pro Tyr Ala Asn Pro Thr Arg Tyr Lys Phe His Asp Trp
1               5                   10                  15

<210> SEQ ID NO 5
<211> LENGTH: 20
<212> TYPE: PRT
<213> ORGANISM: Artificial sequence
<220> FEATURE:
<223> OTHER INFORMATION: Peptide, clone 1.9

<400> SEQUENCE: 5

Asp His Trp Val Trp Gly Trp Asn Tyr Gln Tyr Gln Pro Gln Glu Trp
1               5                   10                  15
```

-continued

```
His Thr Glu Ser
            20

<210> SEQ ID NO 6
<211> LENGTH: 20
<212> TYPE: PRT
<213> ORGANISM: Artificial sequence
<220> FEATURE:
<223> OTHER INFORMATION: Peptide, clone 4.10

<400> SEQUENCE: 6

Asn Gly Tyr Trp Ser Ser Gln Gln Tyr Met Gln Gln Ala Pro Met Pro
1               5                   10                  15

Trp Arg Ile Pro
            20
```